United States Patent
Tsukamoto et al.

[11] Patent Number: 6,134,394
[45] Date of Patent: Oct. 17, 2000

[54] IMAGE FORMING APPARATUS FOR DETECTING VISCOSITY OF A LIQUID TYPE DEVELOPER BY UTILIZING A DEVELOPER DENSITY DETECTING DEVICE

[75] Inventors: Takeo Tsukamoto; Yusuke Takeda, both of Kanagawa-ken, Japan

[73] Assignee: Ricoh Company, Ltd., Tokyo, Japan

[21] Appl. No.: 09/353,778

[22] Filed: Jul. 15, 1999

Related U.S. Application Data

[62] Division of application No. 08/971,898, Nov. 17, 1997.

[30] Foreign Application Priority Data

Jun. 19, 1997 [JP] Japan ................................. 9-177840

[51] Int. Cl.[7] ........................................... G03G 15/10
[52] U.S. Cl. ........................... 399/30; 73/54.15; 73/54.18; 118/689; 399/57
[58] Field of Search ................................. 399/30, 57, 58; 118/689; 73/54.01, 54.02, 54.15, 54.18

[56] References Cited

U.S. PATENT DOCUMENTS

| | | | |
|---|---|---|---|
| 3,635,678 | 1/1972 | Seitz et al. ............................. | 73/54.15 |
| 5,003,352 | 3/1991 | Duchesne et al. ..................... | 399/238 |
| 5,394,739 | 3/1995 | Garvey, III et al. ................. | 73/54.18 X |
| 5,598,251 | 1/1997 | Parish et al. ............................. | 399/30 |
| 5,666,616 | 9/1997 | Yoshino et al. ......................... | 399/240 |
| 5,737,666 | 4/1998 | Lior et al. ................................ | 399/57 |

*Primary Examiner*—William J. Royer
*Attorney, Agent, or Firm*—Oblon, Spivak, McClelland, Maier & Neustadt, P.C.

[57] ABSTRACT

An image forming apparatus having an improved developer density detecting device for detecting density of a liquid type developer without using an optical sensor. Density of the liquid type developer is detected based upon viscosity of the liquid type developer, which is obtained by sensing pressures, for example, of the liquid type developer sent by a pump and flowing through a developer circulating pipe and applying pressure data obtained by sensing pressures to a predetermined formula. The viscosity can also be obtained by dropping a steel ball, or moving a steel ball, through the liquid type developer and measuring an induced current in a coil based on movement of the steel ball. The viscosity can also be obtained by measuring torque of a device rotating with the liquid type developer.

21 Claims, 20 Drawing Sheets

IMAGE FORMING APPARATUS FOR DETECTING VISCOSITY OF A LIQUID TYPE DEVELOPER BY UTILIZING A DEVELOPER DENSITY DETECTING DEVICE This application is a Division of Ser. No. 08/971,898 filed Nov. 17, 1997.

BACKGROUND OF THE INVENTION

1. Field of the Invention

The present invention generally relates to an image forming apparatus, and in particular to a developer density detecting device for detecting density of a liquid type developer having high viscosity which is utilized in a developing device for developing a latent image formed on an image carrier.

2. Description of the Background

In a background image forming apparatus having a developing device for developing a latent image formed on an image carrier with a liquid type developer, a density of the liquid type developer is detected generally by an optical sensing device including a light emitting element for emitting a light beam and a light sensing element. Die light sensing element receives the light beam emitted from the light emitting element after passing through a liquid type developer existing between the light emitting element and the light sensing element.

In such an optical sensing device, the light sensing element generates a voltage signal indicative of an intensity of the light beam received by the light sensing element, which corresponds to a density of the liquid type developer existing between the light emitting element and the light sensing element which receives a light beam emitted from the light emitting element after passing through the liquid type developer. Thereby, the weaker the light beam received by the light sensing element, the higher the density of the liquid type developer.

Further, a background liquid type developer is always stirred by a fan or the like disposed in a developing device so as to eliminate unevenness thereof during an operation of an image forming apparatus. However, even if such a liquid type developer is always circulated by a fan or the like as described above, a density of such a liquid type developer may not be precisely detected by the background optical sensing device when an image forming apparatus operates for a long time, since a quantity of liquid type developer having a high viscosity adheres to the light sensing element for sensing the light beam over time, or a quantity of the liquid type developer drifts at a position between the light emitting element and the light sensing element over time. As a result, an optical beam emitted by the light emitting element is excessively prevented from arriving at the light sensing element by the liquid type developer adhering to the light sensing element and/or drifting between the light emitting element and the light sensing element. As a result, an actual density of a liquid type developer is not accurately detected.

Further, density detection of a liquid type developer by the background optical sensing device is not entirely stable during a long operation of an image forming apparatus due to variations in a level of adhering of the liquid type developer to a light sensing element or a level of drifting thereof at a position between a light emitting element and a light sensing element.

Further, since, in recent years, a darker liquid type developer has been used in an image forming apparatus, in a copier or a printer, for example, having a large CPM (copy per minute), occasions of the liquid type developer adhering to a light sensing element and/or drifting thereof at a position between the light emitting element and the light sensing element is increasing.

Further, a light sensing element of such an optical sensing device generates a different voltage when a different color liquid type developer, a blue liquid type developer for example, is used since a difference exists in the amount of light beam passage through liquid type developer of different colors. Accordingly, if a color of a liquid type developer is changed, a voltage generated by a light sensing element needs to be adjusted to enable using a common control device as previously used for a different color liquid type developer. Therefore, an optical sensing device is generally not suitable for detecting a liquid type developer when an image forming apparatus changes a color of a liquid type developer.

SUMMARY OF THE INVENTION

The present invention has been made in view of such problems and to address and resolve such problems. Accordingly, it is ore object of the present invention to provide a novel image forming apparatus having a developer density detecting device for detecting density of a liquid type developer having high viscosity, and which is capable of avoiding a problem that precise detection of density of a liquid type developer is not obtained by an optical sensing device.

It is another object of the present invention to solve the above-mentioned problems while obtaining stable detection of a liquid type developer having high viscosity during a long time of operation of an image forming apparatus without using an optical sensor.

It is still another object of the present invention to solve the above-mentioned problems while eliminating occasions for a liquid type developer having high viscosity to adhere to a light emitting element or to drift at a position between the light emitting element and a light sensing element even if a darker liquid type developer is used in an image forming apparatus having a large CPM.

It is still another object of the present invention to solve the above-mentioned problems while enabling a precise detection of a liquid type developer having high viscosity without using an optical sensor even when a different color of a liquid type developer is used in an image forming apparatus.

To achieve the above and other objects, an image forming apparatus is improved with a developer density detecting device for detecting density of a liquid type developer having high viscosity without using an optical sensor. In an improved developer density detecting device, density of a liquid type developer is detected based upon viscosity thereof which is obtained by sensing pressures of a liquid type developer flowing in a developer circulating pipe, and referring to relations between viscosity of a liquid type developer and density thereof.

Further, density of a liquid type developer can be detected based upon viscosity which is measured by sensing a time in which a steel ball sinking in a liquid type developer starts falling from a seal of a developer density detecting box and arrives at a bottom thereof, or measuring an induced current in a coil when the steel ball falls through the liquid type developer, and referring to relations between viscosity of a liquid type developer and density thereof.

Further, density of a liquid type developer can be detected based upon viscosity thereof which is obtained by sensing a resisting force of a liquid type developer against a steel ball sinking in the liquid type developer when the steel ball moves the liquid type developer or measuring a moving distance of the steel ball when the steel ball is pushed by a predetermined force, and referring to relations between viscosity of a liquid type developer and density thereof.

Further, density of a liquid type developer can be detected based upon viscosity thereof which is obtained by sensing frequency of a motor for rotating a fan sinking in liquid type developer when the motor is driven, and referring to relations between viscosity of a liquid type developer and density thereof.

Further, density of a liquid type developer can be detected based upon viscosity thereof which is obtained by sensing pressure of a liquid type developer when a liquid type developer is moved by a fan rotated by a motor to which a predetermined electricity is supplied, and referring to relations between viscosity of a liquid type developer and density thereof.

BRIEF DESCRIPTION OF THE DRAWINGS

A more complete appreciation of the present invention and many of the attendant advantage thereof will be readily obtained as the same becomes better understood by reference to the following detailed description when considered in connection with the accompanying drawings, wherein.

DESCRIPTION OF THE PREFERRED EMBODIMENTS

Hereinafter, an image forming apparatus to which the present invention is adopted is explained in detail referring to FIG. 1.

Figure 1:
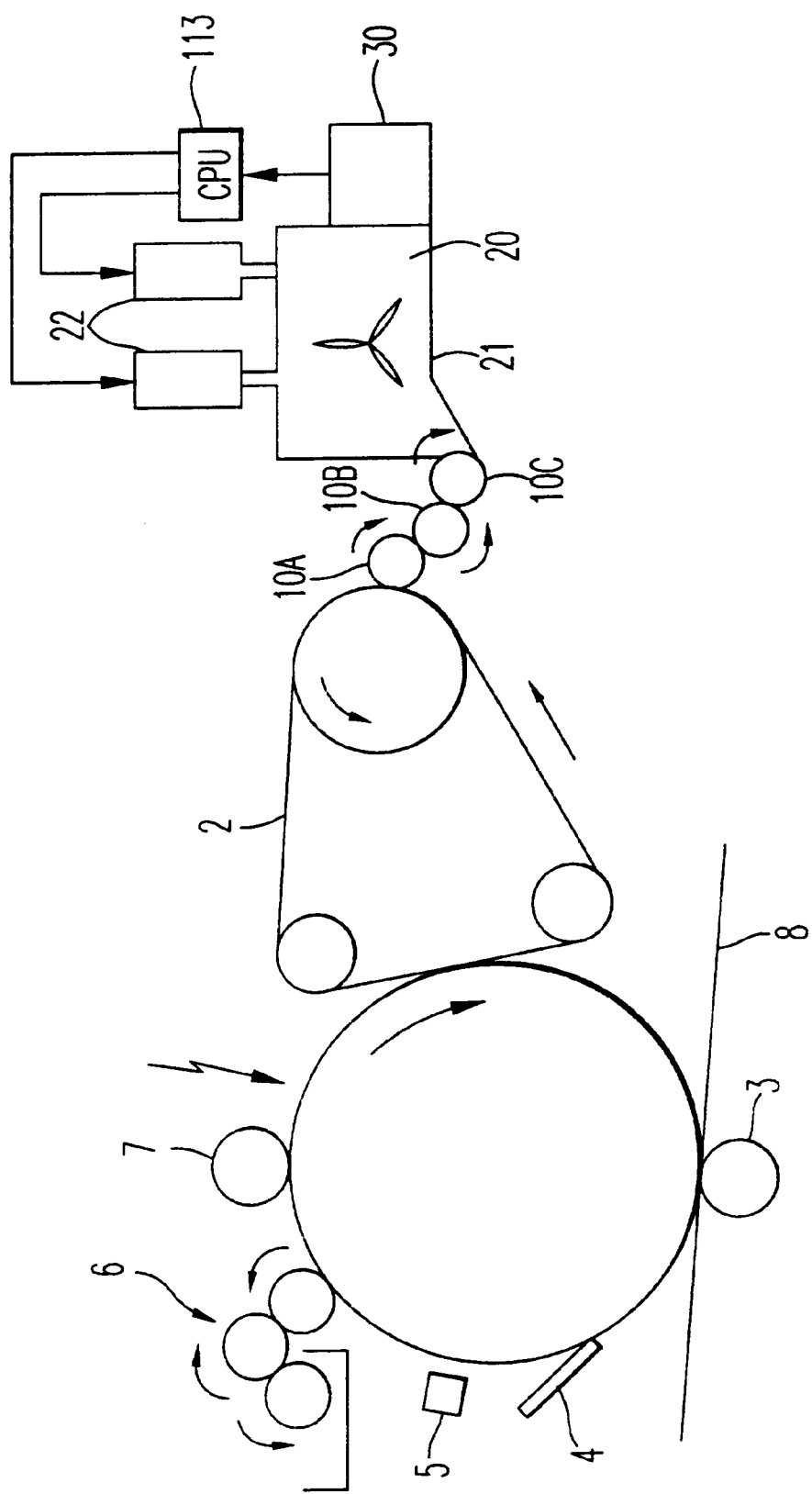
FIG. 1 is a schematic cross sectional view of an image forming apparatus to which a developer density detecting device of the present invention is adopted.

As shown in FIG. 1, an image forming apparatus of the present invention includes a photoconductive drum 1 (hereinafter referred as a PC drum 1) for forming a latent image thereon and a developing belt 2 for developing the latent image formed on the PC drum 1 by circulating in contact with a periphery of the PC drum 1. The image forming apparatus further includes, respectively formed around the PC drum 1, a transfer roller 3 for transferring a toner image formed on the PC drum 1 onto a sheet 8, a cleaning blade 4 for cleaning the PC drum 1 and which contacts the PC drum 1 with a predetermined pressure, a discharge lamp 5 for optically discharging an electric charge remaining on the PC drum 1 after cleaning of the PC drum 1, a pre-wet roller 6 for applying a pre-wet liquid onto the PC drum 1, and a discharging roller 7 for discharging an electric charge having a predetermined polarity. A developer tank 21 contains a liquid type developer for developing the latent image formed on the PC drum 1, developer applying rollers 10a, 10b and 10c apply a liquid type developer contained in the developer tank 21 to the developing belt 2, a developer supplying tank 22 including two small tanks respectively having a lighter developer or a darker developer therein respectively supplies either the lighter developer or the darker developer to the developing tank 21, a density detecting device 30 detects a density of a liquid type developer 20, and a CPU (central processing unit) controls a developing device having the developer density detecting device 30.

A liquid type developer 20 contained in the developer tank 21, which is an object of density detection, has a high viscosity of more than 1000 centimeter-stokes (1000 cSt), a glycerin like developer for example, and which is composed of a resolution material and toner particles dispersed in the resolution material. The developer applying rollers 10a, 10b, and 10c are disposed almost on a line and between the developing belt 2 and the developer tank 21 and respectively contact each other. The roller 10a contacts the developing belt 2 at an opposite side to the PC drum 1 through the developing belt 2. The roller 10c is disposed in an exit opening of the developer tank 21 to contact the liquid type developer 20 contained in the developer tank 21 and to feed the liquid type developer 20 to the roller 10b by rotation.

During passing through the rollers 10a, 10b and 10c, the liquid type developer 20 thereon becomes lighter to form a thin film and is transferred onto the developing belt 2 rotating in contact with the roller 10a. Since a thin film of the liquid type developer 20 is transferred by the roller 10a, another thin film of a liquid type developer is formed on the developing belt 2 after transferring of the liquid type developer 20 from the roller 10a. A pre-wet liquid is applied by the pre-wet roller 6 when the pre-wet roller 6 rotates with the PC drum 1, to form a pre-wet liquid film on a surface of the PC drum to thereby avoid soiling of a copy sheet 8 with unnecessary toner when the toner image formed on the PC drum 1 is transferred onto the copy sheet 8.

Hereinafter, an operation of an image forming process of the image forming apparatus having the above described devices is explained.

A periphery of the PC drum 1 is discharged by discharging roller 7 with an electric charge having a predetermined polarity, and a latent image is formed thereon by a conventional latent image forming device. The latent image is developed by a liquid type developer 20 in a state of a film which is formed on the developing belt 2 rotating in contact with the PC drum 1 with a certain pressure. A toner image is transferred onto a copy sheet 8 passing between the PC drum 1 and the transfer roller 3. The copy sheet 8 then having a toner image thereon is fixed by a fixing device (not shown) and is ejected to an output side of the image forming apparatus. After transferring of the toner image onto the copy sheet 8, residual toner remains on the PC drum 1 and is scrapped off by cleaning blade 4 which contacts the PC drum 1. A surface of the PC drum 1 is optically discharged by the discharge lamp 5 for eliminating an electrostatic charge remaining on the PC drum 1 to initialize the PC drum 1 for a next image forming process.

A developer density detecting device 30 is employed to detect density of a liquid type developer 20 for developing a latent image formed on the PC drum 1 and which generates a signal indicative of a density thereof to be output to a CPU 113. The CPU 113 controls the developer supplying tank 22 to selectively supply either a darker developer or a lighter developer to the developing tank 21 to maintain a density of a liquid type developer 20 contained in developing tank 21 within the a predetermined density range in a manner that if the liquid type developer 20 is lighter than the predetermined density range, the darker liquid type developer is supplied to the developing tank 21, whereas if a liquid type developer 20 is darker than the predetermined density range, the lighter liquid type developer is supplied to the developing tank 21.

Hereinafter, a preferred embodiment of the present invention is described referring to FIGS. 2 to 8, in which an identical reference numeral indicates identical or corresponding parts.

Figure 2:
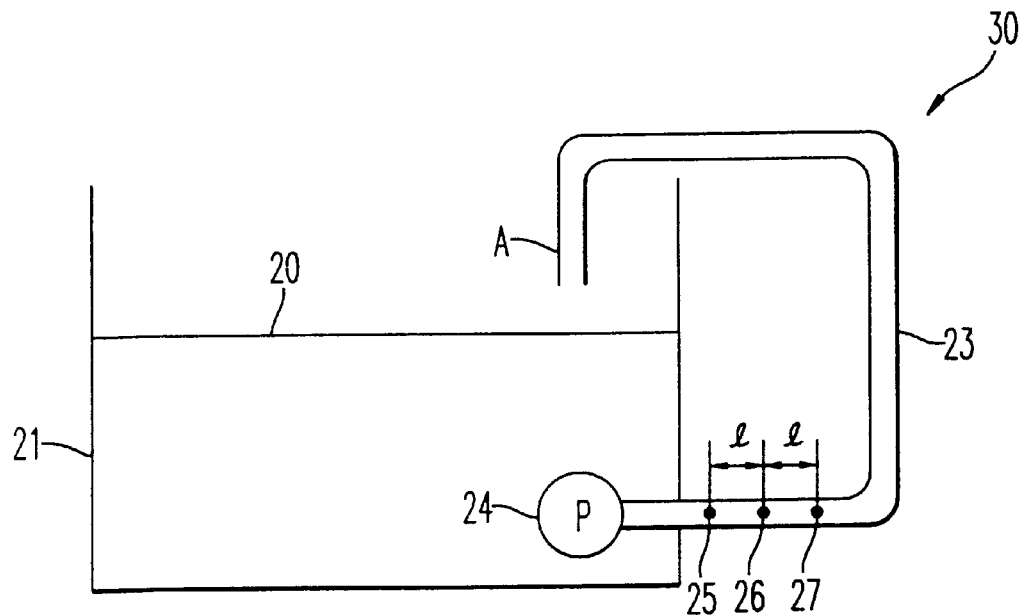
FIG. 2 is a schematic cross sectional view of a developer density detecting device of the present invention which is to be adopted to an image forming apparatus shown in FIG. 1.

An improved developer density detecting device for detecting density of a liquid type developer is illustrated in FIG. 2, in which developer density is detected by measuring viscosity of a liquid type developer 20 flowing in a developer circulating pipe with pressure sensors.

As shown in FIG. 2, the developer density detecting device 30 is connected to a developer tank 21 disposed at a developing station of an image forming apparatus as shown in FIG. 1 to detect density of a liquid type developer 20 contained in the developer tank 21. The developer density detecting device 30 includes a developer circulating pipe 23 for circulating the liquid type developer 20. The circulating pipe 23 is disposed in a state that one end connects with a bottom of the developer tank 21 and another end is positioned above a surface of the liquid type developer 20 contained in the developer tank 21, thereby forming a U-shape. A pump 24 sends the liquid type developer 20 contained in the developer tank 21 to the developer circulating pipe 23 which is disposed at an entrance thereof and three pressure sensors 25, 26 and 27 respectively sense pressure of the liquid type developer 20 passing through each of the sensors 25, 26 and 27 respectively disposed with a predetermined interval to a horizontal portion of the developer circulating pipe 23. As shown in FIG. 2, the liquid type developer 20 sent into the developer circulating pipe 23 by the pump 24 is further sent and finally returns to the developer tank 21 from above thereof through an exit of the developer circulating pipe 23, thereby circulating the liquid type developer 20.

To obtain precise detection, since a pressure sensor acts under an influence of gravity if disposed in a vertical portion of a developer circulating pipe 23, three pressure sensors 25, 26 and 27 are respectively disposed at a horizontal portion of the developer circulating pipe 23 to avoid the influence of gravity. Each of the pressure sensors 25, 26 and 27 respectively generates and sends a pressure signal indicative of pressure of the liquid type developer 20 passing through each of the sensors 25, 26 and 27 to CPU 113 as shown in the FIG. 1.

Figure 4:
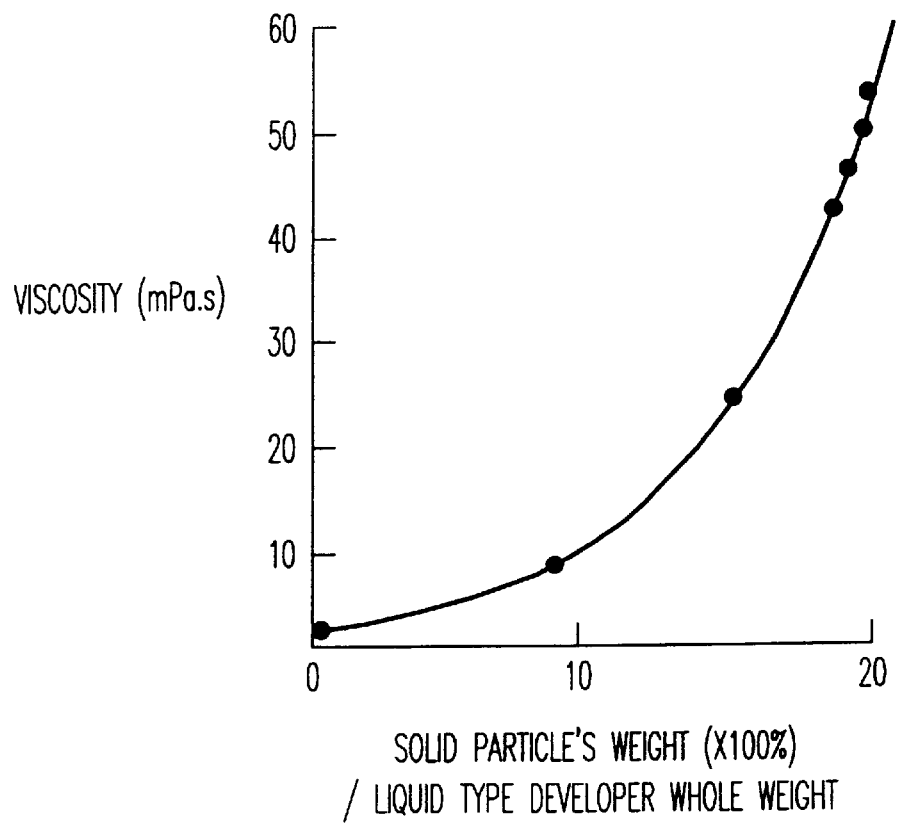
FIG. 4 is a graph showing relations between viscosity and density of a liquid type developer which is obtained experimentally.
Figure 5:
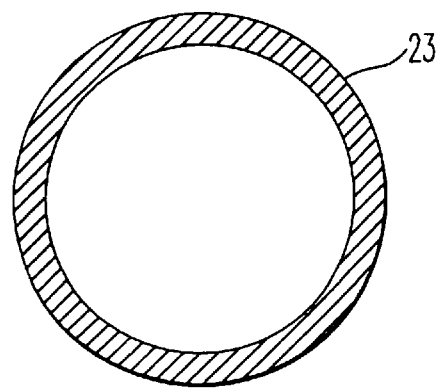
FIG. 5 is a cross sectional view of a developer circulating pipe for use in a developer density detecting device as shown in FIG. 2.
Figure 6:
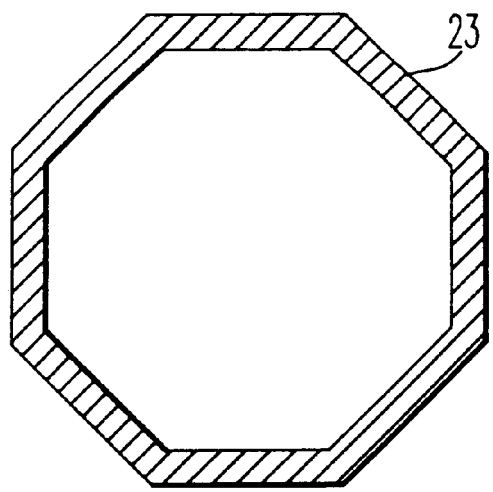
FIG. 6 is a cross sectional view of another developer circulating pipe for use in the developer density detecting device as shown in FIG. 2.
Figure 7:
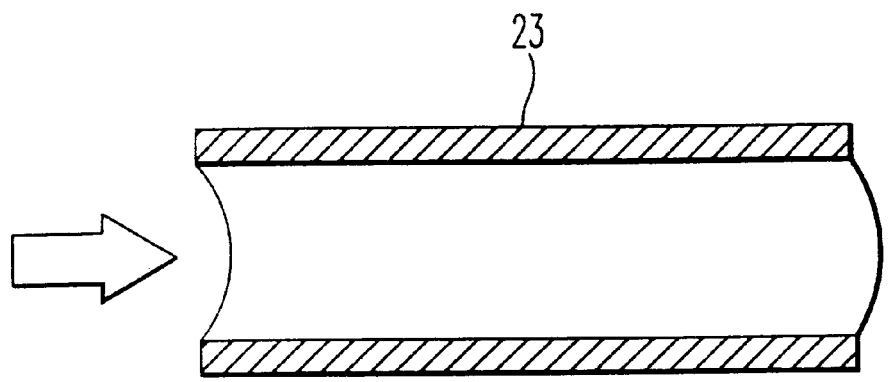
FIG. 7 is a sectional view of a developer circulating pipe for use in a developer density detecting device as shown in FIGS. 5 and 6.
Figure 8:
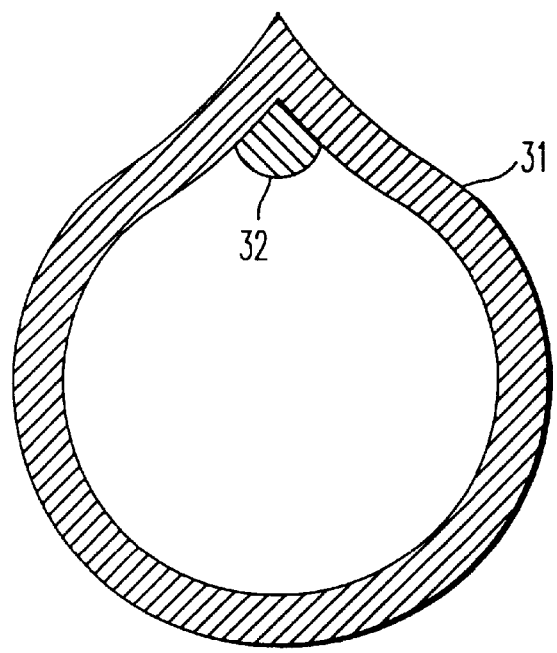
FIG. 8 is a cross sectional view of a developer leading pipe for use in a background developing device which utilizes a liquid type developer.
Figure 9:
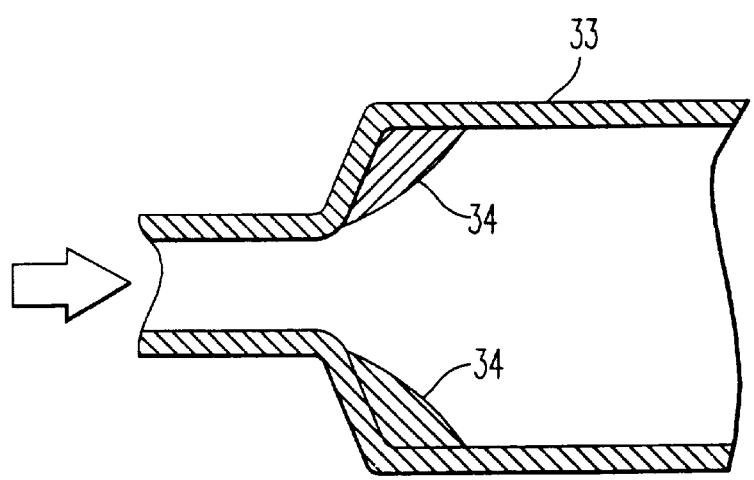
FIG. 9 is a front sectional view of a developer leading pipe for use in a background developing device which utilizes a liquid type developer.

If a section of such a developer circulating pipe 23 has an abnormal shape, as shown in FIGS. 8 and 9, a liquid type developer 20 flowing in the developer circulating pipe 23 tends to adhere (32, 34) to a wall of the developer circulating pipes 31, 33 as shown in FIGS. 8 and 9, and accordingly the liquid type developer 20 does not smoothly flow through the developer circulating pipe 23. Therefore, the developer circulating pipe 23 for circulating a liquid type developer 20 preferably has a cross section of a circle shape or a polygon shape as respectively shown in FIGS. 5 and 6, and which has, a same diameter at every cross section of the developer circulating pipe 23 as shown in FIG. 7, thereby obtaining precise pressure detection. The CPU 113 includes a look-up table showing relations between viscosity of a liquid type developer and density thereof as shown in FIG. 4 for converting viscosity data into density data. The developer density detecting device includes CPU 113 for calculating viscosity of a liquid type developer 20 based upon pressure signals respectively sent by pressure sensors 25, 26 and 27, and determining density of the liquid type developer 20 based upon the viscosity in a manner as described below.

Figure 3:
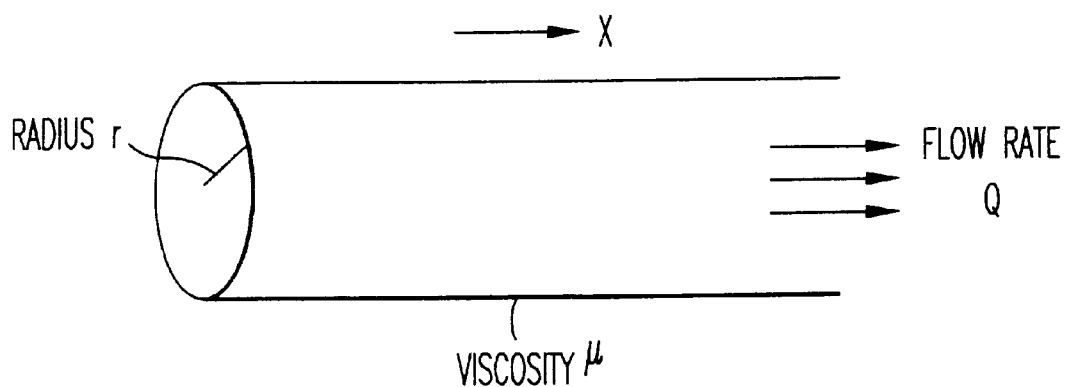
FIG. 3 is a perspective view of a model of a liquid type developer flowing in a developer circulating pipe disposed in a developer density detecting device as shown in FIG. 2.

In a case that a liquid type developer 20 normally flows in a developer circulating pipe 23 as shown in FIG. 3, if viscosity of the liquid type developer 20 is ($\mu$) a radius of the liquid type developer 20 is (r) and a flow rate of the liquid type developer 20 is (Q), the following equation (1) is established.

$$Q = -(dP/dX) \cdot r^4/8\mu \tag{1}$$

In the formula, the parameter X represents a moving length of the liquid type developer 20 in the developer circulating pipe 23 which can be obtained from a length (l) between each of the pressure sensors 25, 26 and 27. The parameter (P) represents pressure of liquid type developer 20 flowing in developer circulating pipe 23 which is obtained by measuring pressure with the three sensors 25, 26, 27 respectively disposed in the developer circulating pipe 23. Thereby, the parameter (dP/dX) represents a pressure gradient between two pressure sensors and which is otherwise calculated by the formula ($_P$–$P_2$)L, or ($P_2$–$P_3$)/L, wherein p represents pressure measured by the first pressure sensor, $P_2$ represents pressure detected by the second pressure sensor and $P_3$ represents pressure detected by the third pressure sensor. The parameter (Q) represents a quantity of a liquid type developer 20 flowing in developer circulating pipe 23 per second. A constant (r) represents a radius of the liquid type developer 20 flowing in the developer circulating pipe 23 and which is also known beforehand from a radius of a section of the developer circulating pipe 23. The CPU 113 shown in FIG. 1 calculates viscosity ($\mu$) of a liquid type developer 20 by setting up simultaneous equations (2), (3) as described below.

$$Q_1 = -(dP_1/dX_1)r^4/8\mu \tag{2}$$

$$Q_2 = -(dP_2/dX_2)r^4/8\mu \tag{3}$$

In the simultaneous equations, ($dP_1/dX_1$) is a pressure gradient between the first pressure sensor and the second pressure sensor, ($dP_2/dX_2$) is a pressure gradient between the second pressure sensor and the third pressure sensor, $Q_1$ is volume of a liquid type developer 20 flowing in the developer circulating pipe 23 per second between the first pressure detecting position and the second pressure detecting position, and $Q_2$ is volume of a liquid type developer 20 flowing in the developer circulating pipe 23 per second between the second pressure detecting position and the third pressure detecting position. Therefore, the equation $Q_1 = -(dP_1/dX_1)r^4/8\mu$ is set up for the liquid type developer 20 flowing between the first pressure sensor and the second pressure sensor, and the equation $Q_2 = -dP_2/dX_2)r^4/8\mu$ is set up for the liquid type developer 20 flowing between the second pressure sensor and the third pressure sensor. Since $Q_1 = Q_2$ due to a same radius of the developer circulating pipe 23, viscosity is obtained by solving the simultaneous equations. Thus, the CPU is able to obtain viscosity ($\mu$) of liquid type developer 20 flowing in the developer circulating pipe 23.

Hereinafter, a principle of detecting density is explained.

Density of a liquid type developer is obtained based upon viscosity in a manner as described below. Since a liquid type developer 20 generally contains a liquid state carrier and solid particles including a paint, a rosin, etc., density of the liquid type developer 20 is generally represented by a ratio between a solid particle's weight and a developer's whole weight, and accordingly is related to viscosity. Relations between viscosity ($\mu$) of a liquid developer and density thereof are obtained from an experiment as shown on a graph as illustrated in FIG. 4. Therefore, if viscosity of a liquid type developer 20 is known, density thereof can be determined by referring to the graph showing the relation between viscosity of liquid type developer and density thereof as shown in FIG. 4.

Hereinafter, an operation of the above described device is explained in detail.

A liquid type developer 20 as an object of density detection is circulated by pump 24 through developer circulating pipe 23. Each of the sensors 25, 26 and 27 respectively disposed in the pipe 23 with a predetermined same interval detects pressure of the liquid type developer 20 flowing through thereof, and outputs a signal indicative of pressure thereof and sends the signal to CPU 113 shown in FIG. 1. The CPU 113 firstly calculates viscosity of the liquid type developer 20 solving simultaneous equations (2) and (3) based upon the pressure signals generated by the pressure sensors 25, 26 and 27, and secondly determines density of the liquid type developer by converting the viscosity data into corresponding density data referring to a look-up table stored in the CPU 113. Thereby, precise density detection for a liquid type developer is obtained without using an optical sensor.

Since pressure of a liquid type developer 20 at an exit (A) shown in FIG. 2 is obtained as an atmospheric pressure, it is sufficient to obtain three pressure data and dispose only two pressure sensors in the developer circulating pipe 23 with a predetermined interval. Therefore, if pressure of a liquid type developer 20 at an exit (A) of a developer circulating pipe 23 is used, the third pressure sensor 27 can be omitted and a same result as described above can be obtained.

Hereinafter, another embodiment of the present invention is explained referring to FIG. 3.

Figure 10:
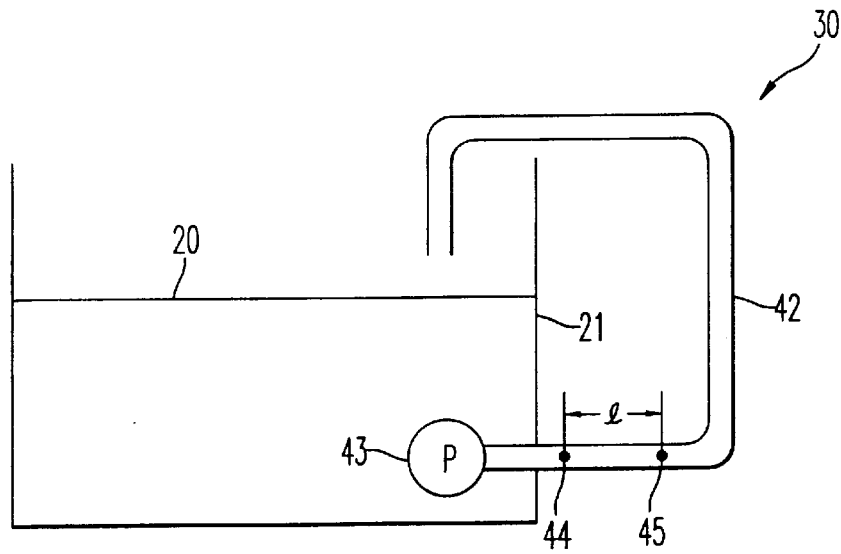
FIG. 10 is a schematic cross sectional view of another developer density detecting device of the present invention in which density of a liquid type developer is detected when a predetermined volume of a liquid type developer is sent into a developer circulating pipe by a pump.

Since a pressure gradient (dP/dX) quoted in formula (1) can basically be obtained by only two pressure information, it is sufficient to calculate viscosity of a liquid type developer 20 referring to formula (1) by using only two pressure sensors 44, 45 disposed in the developer circulating pipe 42 as shown in FIG. 10, if volume of a liquid type developer 20 sent by a pump per second Q is constant. To achieve the above described object, a pair of sensors 44 and 45 are disposed in a horizontal portion of a developer circulating pipe 42 with a predetermined interval I to detect pressure of the liquid type developer 20 which passes through thereof, and a pump 43 is controlled to send a predetermined volume of a liquid type developer 20 per second or to send a certain volume under predetermined pressure per second, and thereby a same result is obtained as described in the above described embodiment. Thus, a minimum number of pressure sensors is used for measuring pressure of a liquid type developer 20 flowing through a developer circulating pipe 42 in this embodiment.

Hereinafter, still another embodiment of the present invention is explained referring to FIG. 11.

Figure 11:
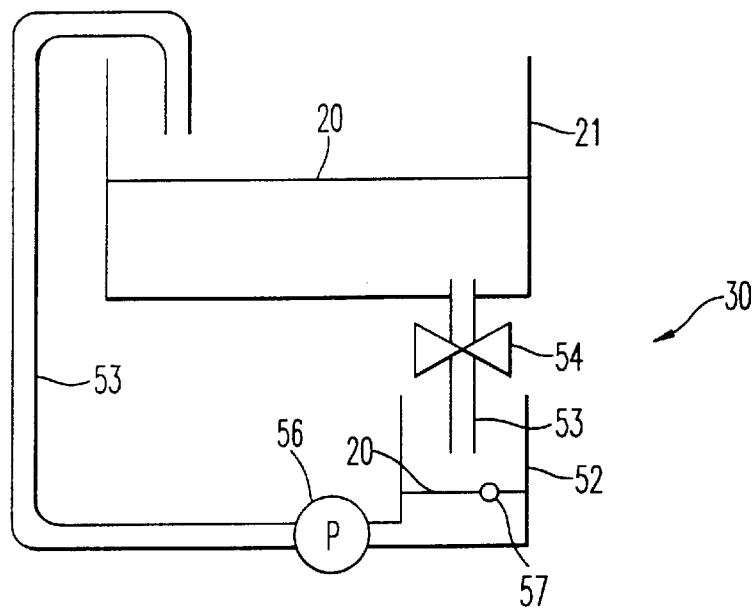
FIG. 11 is a schematic cross sectional view of still another developer density detecting device of the present invention which detects density of a liquid type developer, when a liquid type developer falls through pressure sensors.

An improved developer density detecting device is illustrated in FIG. 11, in which viscosity of a liquid type developer 20 is measured by measuring pressures of liquid type developer 20 falling through a pipe vertically disposed and a quantity flowing through the pipe within a predetermined time. As shown in FIG. 11, a liquid type developer 20 as an object of density detection is contained in a developer tank 21. A developer density detecting device 30 for detecting density of liquid type developer 20 includes an ejecting pipe 53 for ejecting the liquid type developer 20 contained in the developer tank 21. The ejecting pipe 53 is disposed vertically in a state that one end is connected to a bottom of the developer tank 21, thereby ejecting the liquid type developer 20 contained in the developer tank 21 downward by gravity. A valve 54 is provided for allowing or inhibiting passage of a liquid type developer 20 through the ejecting pipe 53 and is mounted at about a middle of the ejecting pipe 53. A measuring tank 52 receives the liquid type developer 20 as an object of density detection from the developer tank 21 through the ejecting pipe 53 when the valve 54 is open and measures newly supplied liquid type developer 20. A returning pipe 55 returns liquid type developer 20 from the measuring tank 55 to the developer tank 21 by connecting both the measuring tank 52 and the developer tank 21.

The developer density detecting device 30 further includes a pump 56 for sending the liquid type developer 20 temporally contained in the measuring tank 52 to the developer tank 21 through the returning pipe 55. The pump 56 is disposed in the returning pipe 55. A floating sensor 57 senses a liquid type developer 20 newly supplied into the measuring tank 52 from the developer tank 21 and outputs a signal indicative of a volume of the liquid type developer 20 newly supplied to CPU 113 shown in FIG. 1. The floating sensor 57 is disposed in the measuring tank 52 and floats on a surface of a liquid type developer 20 contained in the measuring tank 52. A section of the ejecting pipe 53 has a predetermined diameter and is, e.g., a circle shape, as in the section of the developer circulating pipe 23 shown in FIG. 5.

An operation of density detection by such a density detecting device 30 is explained as described below. Both the valve 54 and the pump 56 are controlled such that the valve 54 is open for a predetermined time period while the pump 56 stops sending liquid type developer 20, and thereby a certain volume of a liquid type developer 20 is contained in the measuring tank 52. The floating sensor 57 measures a volume of the liquid type developer 20 newly supplied into the measuring tank 52 within a predetermined time period and generates a signal indicative of the volume thereof. After the predetermined time has elapsed, the valve 54 is closed and the pump 56 starts sending the liquid type developer 20 contained in the measuring tank 52 back to the developer tank 21 through the returning pipe 55.

In such a device, viscosity is calculated in a manner as described below.

When a signal indicative of volume of a liquid type developer 20 newly supplied into the measuring tank 52 is input to the CPU 113 shown in FIG. 1, the CPU 113 calculates a volume of the liquid type developer 20 flowing through the ejecting pipe 53 per second by dividing the volume of the liquid type developer 20 newly supplied into the measuring tank 52 by a predetermined time period. Further, a radius (r) of the ejecting pipe 53 is constant and a pressure of a liquid type developer 20 flowing under gravity at a bottom of the developer tank 21 and a pressure thereof at an exit of the ejecting pipe 53 are respectively obtained as an atmospheric pressure plus hydraulic pressure of a liquid type developer 20 contained in the developer tank 21 ($P_b$) and an atmospheric pressure ($P_a$), and further a length of a portion of the ejecting pipe 53 from the bottom of the developer tank 21 and the exit thereof is l, and thereby (dP/dX) is obtained by a formula ($P_b-P_a$)/l. Thus, the CPU 113 can calculate viscosity $\mu$ referring to the formula (1) by applying the above described known data and a constant to the formula (1).

The CPU 113 then converts the viscosity data of the liquid type developer 20 obtained by referring to the formula (1) into a density data referring to a look-up table showing a relation between viscosity of a liquid type developer and density thereof which is stored in the CPU 113. A device for measuring a flow rate of a liquid type developer 20 flowing through an ejecting pipe 53 (Q) is not limited to the above described device, and another device as explained below can be used.

If a time period in which a predetermined volume of a liquid type developer 20 newly supplied into the measuring tank 52 through ejecting pipe 53 is measured by a timer for example, a flow rate of the liquid type developer flowing through the ejecting pipe 53 (Q) is calculated by dividing the predetermined volume of the liquid type developer 20 by the time period measured by the timer, for example, thereby obtaining a same result.

Hereinafter, still another feature of the present invention is explained referring to FIGS. 12 and 13.

Figure 12:
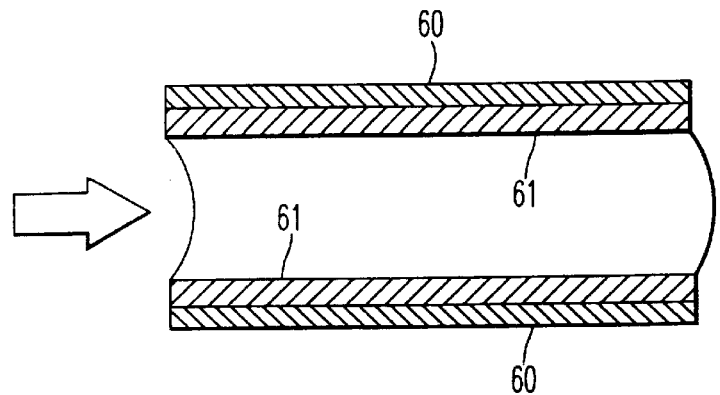
FIG. 12 is a front sectional view of an improved developer circulating pipe for use in a developing device of the present invention.
Figure 13:
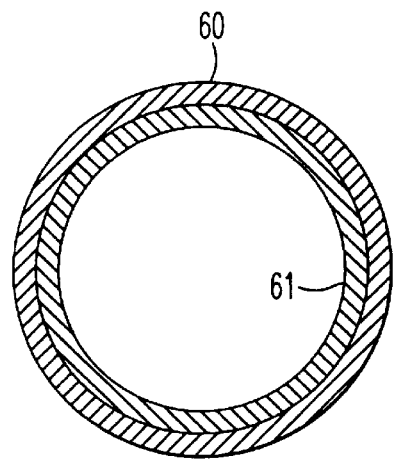
FIG. 13 is a cross sectional view of a developer circulating pipe for use in a developing device for developing with a liquid type developer as shown in FIG. 12.

An improved developer leading pipe 60 for leading a liquid type developer 20 in a use of a developer density detecting device for detecting density of a liquid type developer 20 is shown in FIGS. 12 and 13.

As shown in FIGS. 12 and 13, an oil repelling material 61, a fluoric resin for example, is coated on an inner surface of the developer leading pipe 60. Therefore, when a liquid type developer 20 is lead through the developer leading pipe 60 having an inner surface coated by the oil repelling material 61, solid particles contained in the liquid type developer 20 flowing through the developer leading pipe 60 do not adhere to the inner surface of the developer leading pipe 60, and the liquid type developer 20 does not drift ir the developer leading pipe 60. Accordingly, since the liquid type developer uniformly flows throughout the developer leading pipe 60 due to an oil repelling force of the oil repelling material 61 coated inside the developer leading pipe 60, a predetermined volume thereof is precisely sent or a certain volume of a liquid type developer 20 is sent under predetermined precise pressure by a pump. As a result, pressure of the liquid type developer flowing through the developer leading pipe 60 is precisely measured, and accordingly viscosity is precisely calculated based upon the pressure referring to formula (1), and as a result density of the liquid type developer 20 is also precisely determined based upon the viscosity. Such an improved developer leading pipe 60 can be used as a developer circulating pipe as shown in FIGS. 2 and 3 and an ejecting pipe as shown in FIG. 4, as examples only.

Hereinafter, still another feature of the present invention s explained referring to FIG. 14.

Figure 14:
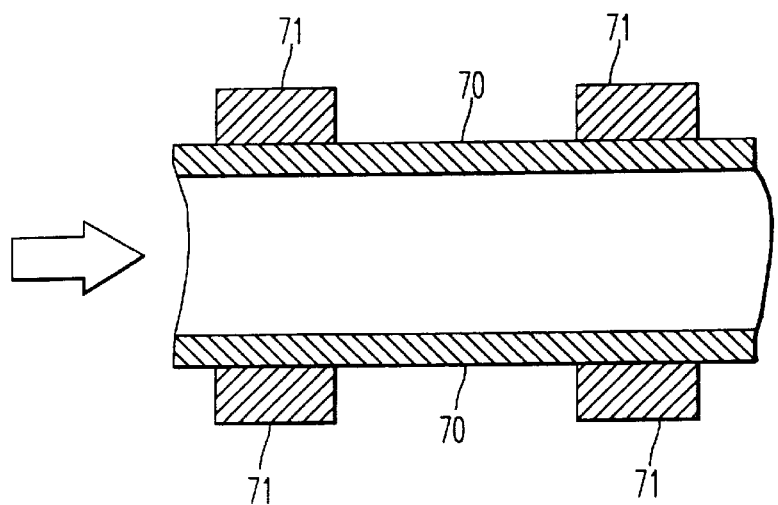
FIG. 14 is a cross sectional view of another improved developer circulating pipe for use in a liquid type developing device for developing with a liquid type developer as shown in FIG. 12.

A further improved developer leading pipe 70 for leading a liquid type developer 20 and which is used in a developer density detecting device for detecting density of a liquid type developer 20 is illustrated in FIG. 14. As shown in FIG. 14, a plurality of vibration generating members 71, supersonic wave generating members for example, are mounted to an outer surface of the developer leading pipe 70. The vibration generating members 71 always or periodically apply predetermined vibrations to the developer leading pipe 70 to avoid solid particles contained in the liquid type developer 20 adhering to a wall of an inner surface of the developer leading pipe when flowing through the developer leading pipe 70, or to forcefully remove solid particles from an inner surface of the developer leading pipe 70 due to vibrations thereof even if the solid particles of the liquid type developer 20 are adhering to the wall of the developer leading pipe 70. Therefore, when a liquid type developer 20 flows through the developer leading pipe 70, solid particles contained in the liquid type developer 20 will not easily adhere to an inner surface of the developer leading pipe 70 or particles are forcefully removed from an inner surface of the developer leading pipe 70.

Accordingly, since the liquid type developer uniformly flows throughout the developer leading pipe 70, a predetermined volume of the liquid type developer is precisely sent or a certain volume of a liquid type developer 20 is precisely sent under predetermined pressure by a pump through the developer leading pipe 70. As a result, a pressure of liquid type developer 20 flowing through the developer leading pipe 70 is precisely measured, and accordingly viscosity of the liquid type developer is precisely calculated based upon the pressure referring to formula (1), and accordingly density of the liquid type developer is also precisely determined based upon the viscosity. Such an improved developer leading pipe 70 can be used as a developer circulating pipe as shown in FIGS. 2 and 3 and an ejecting pipe as shown in FIG. 4, as examples only.

Heretofore, all of the embodiments relate to density detection using pressure sensors for measuring pressures of a liquid type developer 20 flowing in a developer circulating pipe. Hereinafter, another embodiment of the present invention is explained in detail referring to FIGS. 15(*a*) to 21(*b*), in which density of a liquid type developer is detected using a steel ball, which falls through a liquid type developer as an object of density detection.

Figure 15A:
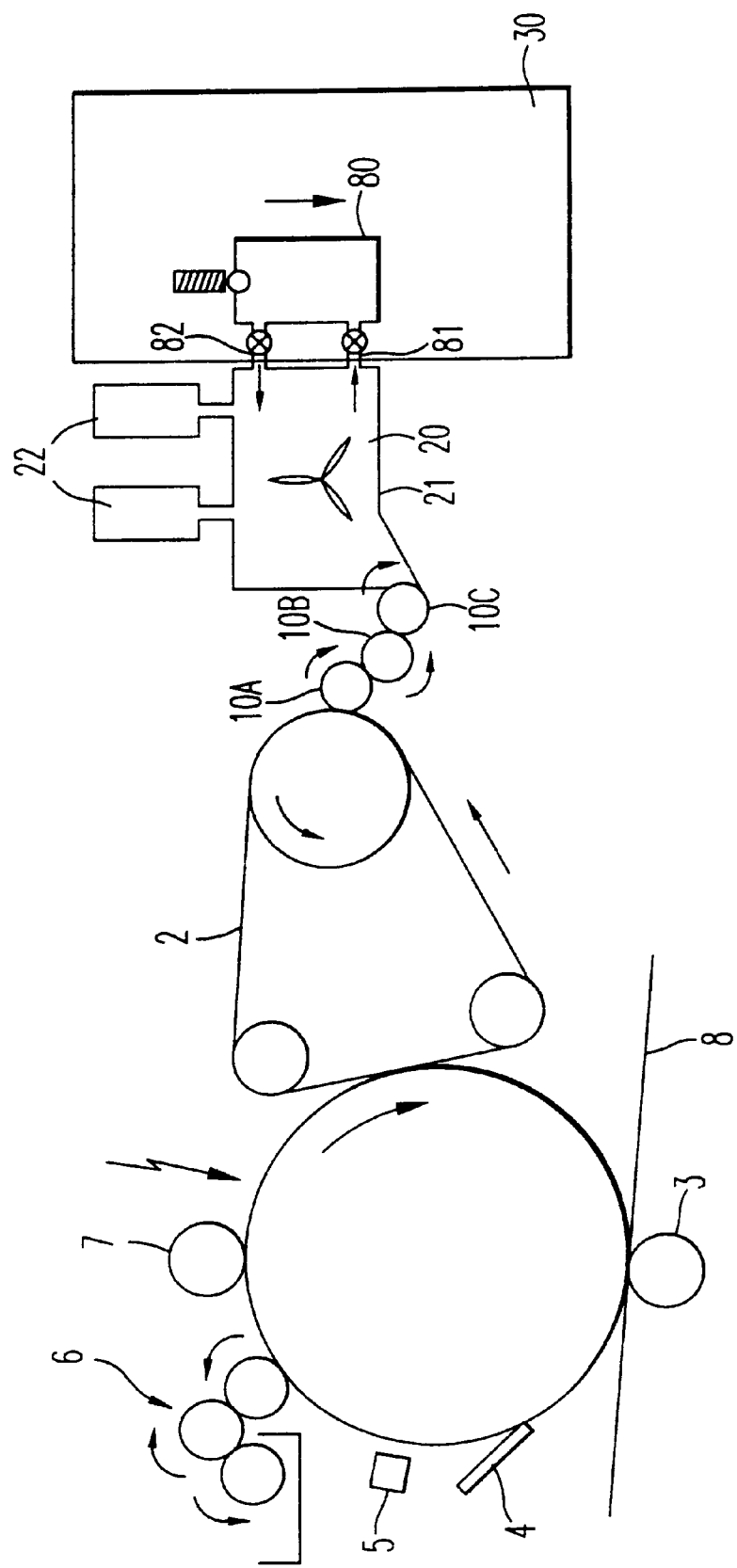
FIG. 15(a) is a perspective cro ;s sectional view of an image forming apparatus having another density detecting device of the present invention which detects density of a liquid type developer by measuring viscosity with a steel ball falling through the liquid type developer.
Figure 15B:
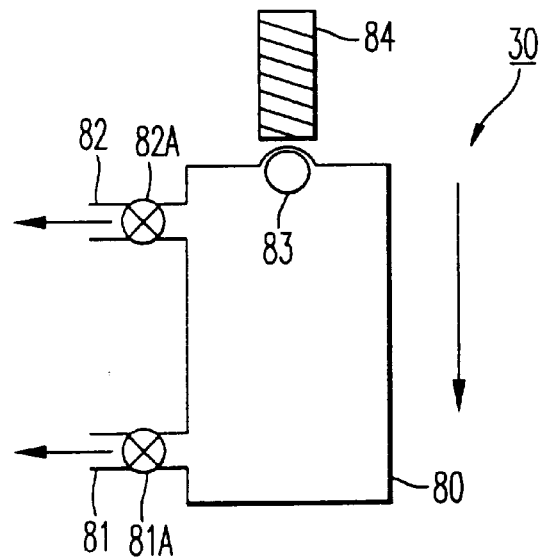
FIG. 15(b) is a cross sectional view of a density detecting device adopted to the image forming apparatus as shown in FIG. 15(a) which illustrates an initial state thereof for detecting density with a steel ball falling through a liquid type developer.

An image forming apparatus employing an improved developer density detecting device 30 is illustrated in FIG. 15(*a*). An improved developer density detecting device 30 adopted to an image forming apparatus is illustrated in FIG. 15(*b*). As shown in FIG. 15(*a*), a developer density detecting box 80 is disposed beside the developer tank 21 which contains a liquid type developer 20 as an object of density detection therein and is connected to the developer tank 21 by both a developer supplying pipe 81 and a developer ejecting pipe 82. A liquid type developer 20 is lead through the developer supplying pipe 81 into the developer density detecting box 80 and is ejected through the developer ejecting pipe 82 after density detection thereof is completed. As shown in FIG. 15(*b*), both valves 81*a* and 82*a* for respectively allowing or inhibiting passage of a liquid type developer 20 are respectively disposed in the developer supplying pipe 81 and the developer ejecting pipe 82.

When both of the valves 81*a* and 82*a* are open, liquid type developer 20 contained in the developer density detecting box 80 is ejected through developer ejecting pipe 82 and developer contained in developer tank 21 is supplied to the developer density detecting box 80 through the developer supplying pipe 81 as shown in FIG. 15(*a*). On the other hand, when both of the valves 81*a*, 82*a* are shut, the liquid type developer 20 contained in the developer density detecting box 80 is isolated from an output side of the developer density detecting box 80 to maintain the liquid type developer contained in the developer density detecting box 80 without being disturbed.

A steel ball 83 is installed in the developer density detecting box 80 and sinks into a liquid type developer 20 contained therein when liquid type developer 20 is supplied into the developer density detecting box 80. A dent is formed at almost a middle portion of an upper wall of the developer density detecting box 80 for accepting a part of the steel ball 83 therein. An electromagnet 84 is disposed above the upper wall of the developer density detecting box 80 and is adjacent to the dent formed on the upper wall thereof to magnetically attract the steel ball 83 when electricity is supplied thereto. The electromagnet 84 magnetically attracts the steel ball 83 toward the dent when electricity is supplied thereto to set an initial state for density detection, and the steel ball 83 is released from the dent when the supply of electricity is stopped.

Figure 16:
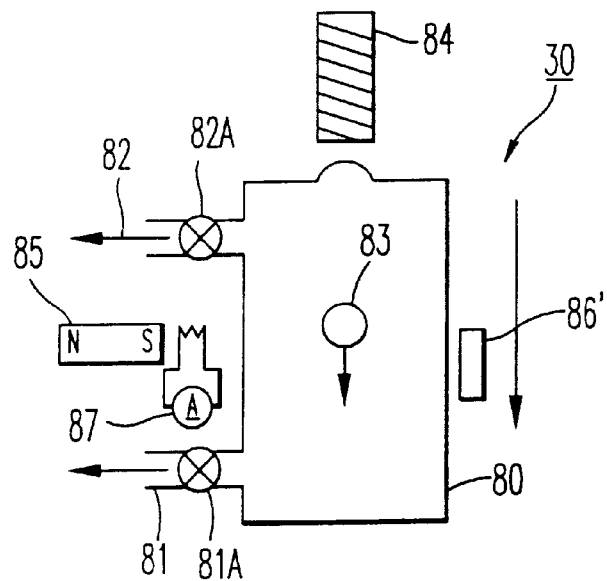
FIG. 16 is a cross sectional view of a developer density detecting device of the present invention which shows a state that a steel ball is falling through a coil wound around the developer density detecting device at a predetermined height.

As shown in FIG. 16, a permanent magnet 85 can be disposed beside the developer density detecting box 80 at a predetermined height and adjacent to a route along which the steel ball 83 falls from the seal of the developer density detecting box 80 to a bottom thereof. As shown in FIG. 16, a coil 86, having a current detector 87 for detecting an induced current is wound around the developer density detecting box 80 and is positioned at a same height as the permanent magnet 85. Therefore, the coil 86 is positioned between the permanent magnet 85 and the steel ball 83 when the steel ball 83 passes past or through the coil 86.

Figure 17A:
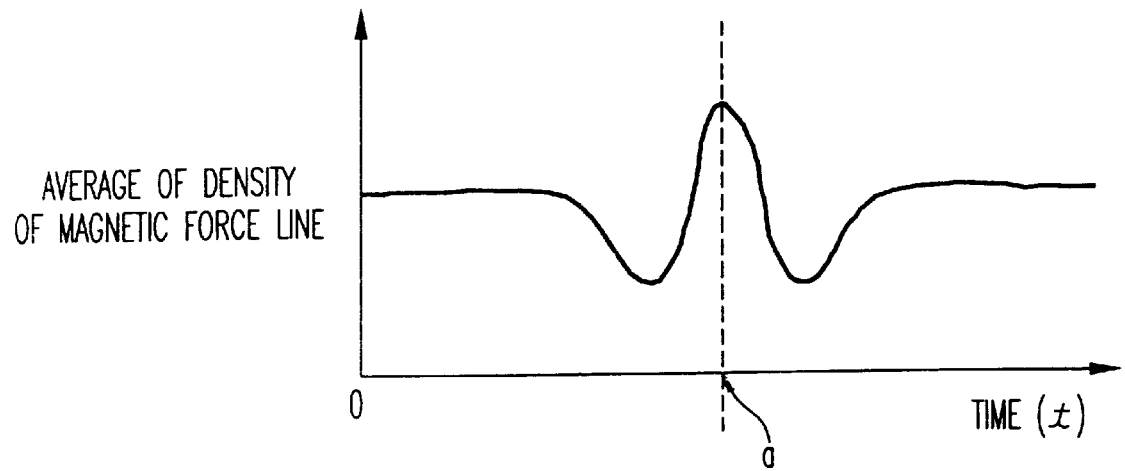
FIG. 17(a) is a graph showing relations between an average of density of a magnetic force line and a time from when a steel ball starts falling to when a steel ball passes through a coil wound around the density detecting device.
Figure 17B:
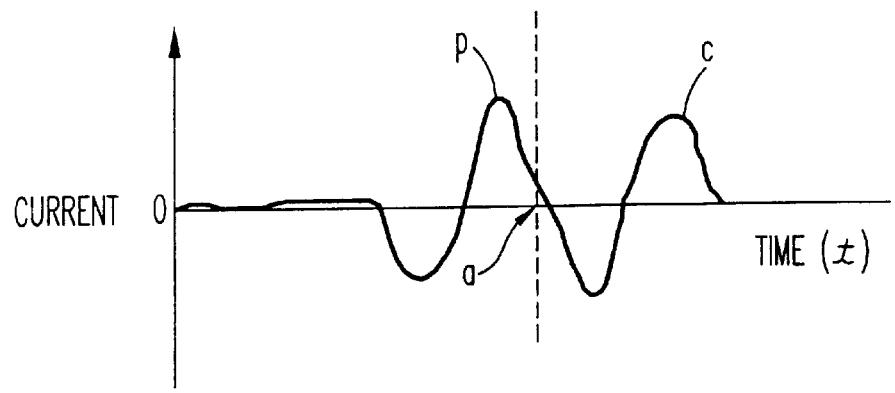
FIG. 17(b) is graph showing relations between a current flowing in a coil and a time from when a steel ball starts falling to when a steel ball passes through a coil wound around the density detecting device.

FIG. 17(*a*) is a graph showing relations between a time from when steel ball 83 gets an initial speed and an average of density of a magnetic force line through the coil 86. FIG. 17(*b*) is a graph showing relations between a time from when a steel ball 83 gets an initial speed and a current flowing through the coil 86 which is produced by a falling movement of the steel ball 83. In both FIGS. 17(*a*) and 17(*b*), a point (a) represents a time when the steel ball 83 just passes through the height where the coil 86 is positioned.

Hereinafter, an operation of density detection of a liquid type developer 20 by using the above described device is explained in detail. Electricity is continuously supplied to the electromagnet 84 for attracting the steel ball 83 into the dent and keeping it therein until density detection starts. Then, the supply of electricity to the electromagnet 84 is stopped to release the steel ball 83 downward from the dent formed on the upper wall thereof to thereby start density detection of the liquid type developer 20. The steel ball 83 released from the attraction of the electromagnet 84 falls with an initial velocity since gravity is larger than a buoyant force of the steel ball 83 sinking in the liquid type developer 20 contained in the developer density detecting box 80. When the steel ball 83 passes through the coil 86 an electric current is induced in the coil 86 since the steel ball 83 disturbs a magnetic field created by the permanent magnet 85. Density of a magnetic force line created by the permanent magnet 85 largely changes when the steel ball 83 passes through the coil 86 as shown in FIG. 17(*a*), and a current introduced in and flowing through the coil 86 become s a peak level before and after the steel ball 83 passes through the coil 86 as shown in the FIG. 17(*b*). Since such a peak current is related to a falling speed of steel ball 83 and the falling speed is also related to viscosity of the liquid type developer 20, if a peak current flowing in the coil 86 is measured, viscosity of liquid type developer 20 can be calculated. The CPU 113, therefore, detects a peak current flowing in the coil 86 and measures viscosity based upon the peak current, and finally determines density based upon viscosity referring to relations between viscosity of a liquid type developer and density thereof as shown in FIG. 4. In the above described density detection, the higher the falling speed of steel ball 83, the lower the density of liquid type developer 20.

It is preferable for measuring density to design a length between the permanent magnet 85 and the coil 86 to be longer than that between the coil 86 and the steel ball 83 passing through the coil 86.

It is also preferable to dispose the permanent magnet 85 so far from a route along which the steel ball 83 falls from a seal of the developer density detecting box 80 to a bottom thereof to avoid an influence of a magnetic force thereof onto a falling movement of the steel ball 83.

Since an area surrounded by both a time axis (t) and current curve (c) is related to a falling speed of the steel ball 83 as shown FIG. 17(*b*), it is also possible to measure viscosity of a liquid type developer 20 by integrating a current having the curve (c) instead of measuring a peak current level as described above. To achieve the above described purpose, an integrator for integrating a current flowing in the coil 86 is disposed in CPU 113 shown in FIG. 1.

Figure 18:
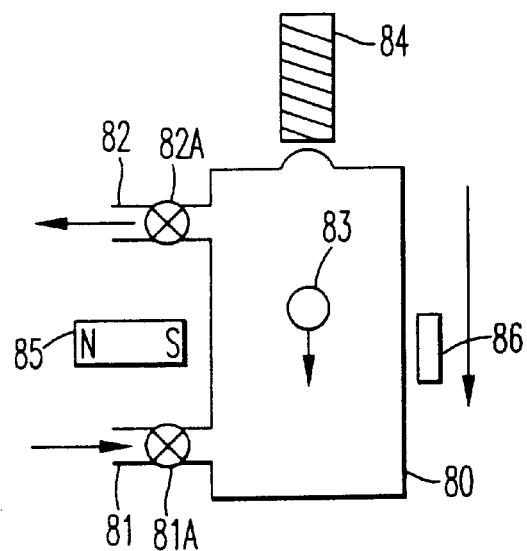
FIG. 18 is a cross sectional view of another developer density detecting device of the present invention which detects density by measuring viscosity with a steel ball falling through a coil disposed beside the developer density detecting device and opposite to a permanent magnet through the developer density detecting device.

As shown in FIG. 18, a coil 86 can be disposed beside the developer density detecting box 80 opposite to the permanent magnet 85 through the developer density detecting box 80 instead of winding a coil around the developer density detecting box 80. In such a slightly modified embodiment, a current is also introduced in coil 86 when steel ball 83 passes through the coil 86 since the steel ball 83 also disturbs a magnetic force line created by permanent magnet 85, and as a result, density of a liquid type developer 20 is also precisely detected in a same manner as described above.

Hereinafter, another embodiment of the present invention is explained referring to FIG. 19.

Figure 19:
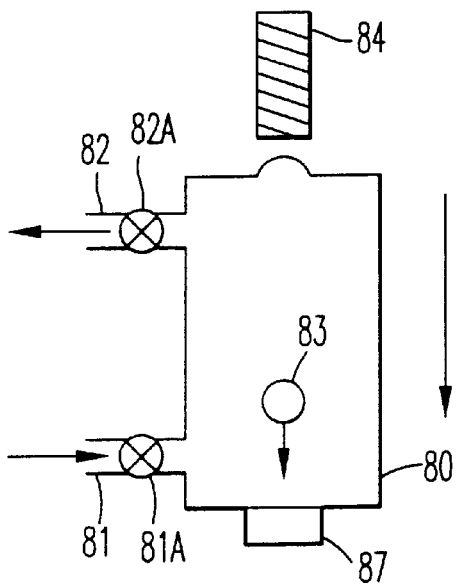
FIG. 19 is a cross sectional view of still another developer density detecting device for detecting density by measuring viscosity with a steel ball in which a piezoelectric element is disposed at a bottom of a developer density detecting device to detect arrival of the steel ball.

An improved developer density detecting device of the present invention is illustrated in FIG. 19 in which the permanent magnet 85 and the coil 86 as described in the above embodiment are not utilized.

As shown in FIG. 19, a piezoelectric element 87 is disposed at a bottom of a developer density detecting box 80 and generates a signal when a steel ball 83 falling through a liquid type developer 20 contained in the developer density detecting box 80 collides therewith. A time period from when the steel ball 83 gets an initial speed at a seal of the developer density detecting box 80 until it reaches the piezoelectric element 87 disposed at the bottom thereof can be measured by detecting the time of supplying electricity to electromagnet 84 and when the steel ball 83 collides with the piezoelectric element 87. The time period is in proportion to a falling speed of the steel ball 83 and the falling speed is related to viscosity of a liquid type developer 20 contained in the developer density detecting box 80. Therefore, if the time period from when the steel ball 83 gets an initial speed until it reaches the bottom of the developer density detecting box 80 is measured, viscosity of liquid type developer 20 is obtained, and accordingly, density thereof is also obtained referring to relations between viscosity of the liquid type developer and density thereof as shown in FIG. 4.

In such a density detection, the higher the density of the liquid type developer 20, the longer the time period fr6m when steel ball 83 gets an initial speed until it reaches a bottom of the developer density detecting box 80. Density is, therefore, detected based upon such a time period by using such a developer density detecting device.

It is, however, difficult for the above described density detecting device to repeatedly detect density of liquid type developer 20 contained in a developer density detecting box 80, since the steel ball 83 can not move under influence of gravity after it arrives at the bottom of the developer density detecting box 80.

Hereinafter, still another embodiment of the present invention is described referring to FIG. 20, in which such a problem is resolved.

As shown in FIG. 20, a developer density detecting box 80 having a dent at a seal thereof is connected to a developer tank 21 by both a developer supplying pipe 91 and a developer ejecting pipe 92 containing respective valves 91*a* and 92*a*. Both the developer supplying pipe 91 and the developer ejecting pipe 92 are made of an elastic material to expand when pulled by an outer force. A swinging motor (not shown) for swinging the developer density detecting box 80 to be upside down is also employed. An electromagnet 84 is integrally connected to the developer density detecting box 80.

Figure 20A:
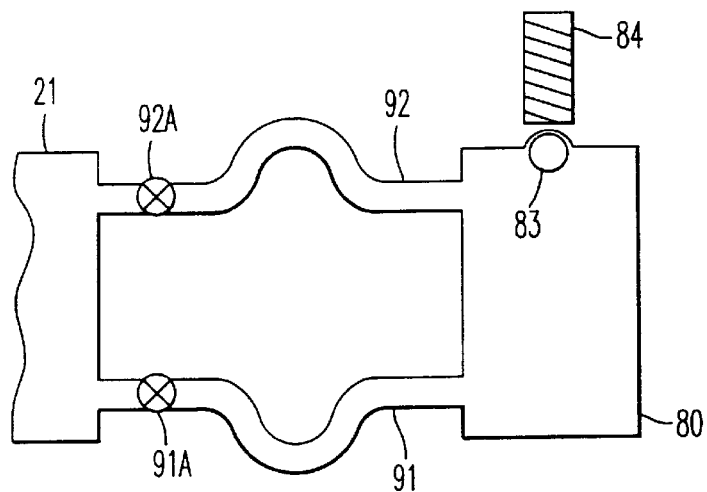
FIGS. 20(a)–20(c) are cross sectional views of still another developer density detecting device of the present invention which detects density by measuring viscosity with a steel ball falling through liquid type developer as an object of density detection.
Figure 20B:
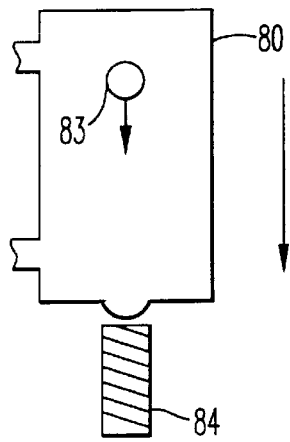
Figure 20C:
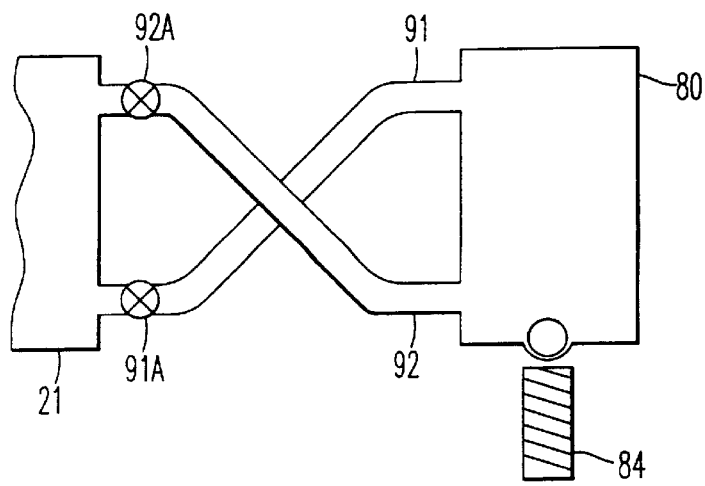

When density detection of a liquid type developer 20 contained in a developer density detecting box 80 is repeated, used liquid type developer 20 remaining in the developer density detecting box 80 is ejected therefrom through the developer ejecting pipe 92 and new developer is supplied into the developer density detecting box 80 through the developer supplying pipe 91. Density detection starts when supplying of electricity to electromagnet 84 is stopped to release the steel ball 83 downward from a seal dent formed on an upper wall of the developer density detecting box 80. Before the steel ball 83 arrives at a bottom of the developer density detecting box 80, the swinging motor (not shown) is driven to swing the developer density detecting box 80 to be upside down in a state that both the developer supplying pipe 91 and the developer ejecting pipe 92 connect with the developer density detecting box 80 as shown in FIG. 20(c). When the swinging motor swings the developer density detecting box 80, both the developer supplying pipe 91 and the developer ejecting pipe 92 are twisted. Both the developer supplying pipe 91 and the developer ejecting pipe 92 however are smoothly twisted and function in a same manner as before twisting thereof, since both the developer supplying pipe 91 and the developer ejecting pipe 92 are made of an elastic material.

Since it is connected to the developer density detecting box 80, the electromagnet 84 swings together with the developer density detecting box 80. Since electricity is not supplied to the electromagnet 84 during swinging of the developer density detecting box 80, steel ball 83 is free from an influence of an attraction of the electromagnet 84 and gravity is larger than a buoyant force for the steel ball 83, and accordingly the steel ball 83 falls through the liquid type developer 20 contained in the developer density detecting box 80 as shown in FIG. 20(b). The steel ball 83 then reaches the dent then positioned at a bottom of the developer density detecting box 80 as shown in FIG. 20(c). At this moment, density detection of liquid type developer 20 is completed and viscosity is measured based upon a time period from when the steel ball 83 gets an initial speed until it reaches the dent then positioned at a bottom thereof as described before. After the steel ball 83 has reached the dent positioned at the bottom of the developer density detecting box 80 being once upside down, electricity is supplied to the electromagnet 84 then positioned below the developer density detecting box 80 to keep the steel ball 83 in the dent as shown in FIG. 20(c), and then the swinging motor (not shown) is driven to swing the developer density detecting box 80 and the electromagnet 84 in a reverse direction to return the developer density detecting box 80 to an initial position thereof, as shown in FIG. 20(a), to prepare for a next density detection of liquid type developer 20. The next density detection is executed in a same manner as described above. Therefore, a desired number of density detection operations is repeated by the above described device of the present invention.

Hereinafter, still another embodiment of the present invention is explained referring to FIGS. 21(a) and 21(b). An improved developer density detecting device is illustrated in FIGS. 21(a) and 21(b), in which density detection of a liquid type developer 20 is repeated by an improved developer density detecting device.

Figure 21A:
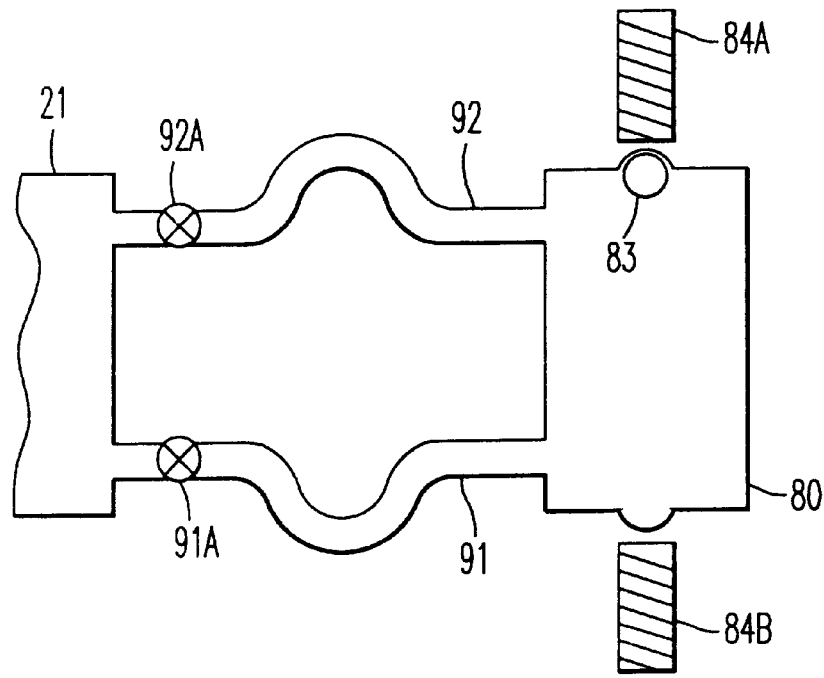
FIGS. 21(a) and 21(b) are sectional views of still another developer density detecting device of the resent invention which is a slightly modified developer density detecting device as shown in FIG. 20, in which a pair of electromagnet coils are respectively disposed above an upper wall of the density detecting device and below a lower wall thereof.
Figure 21B:
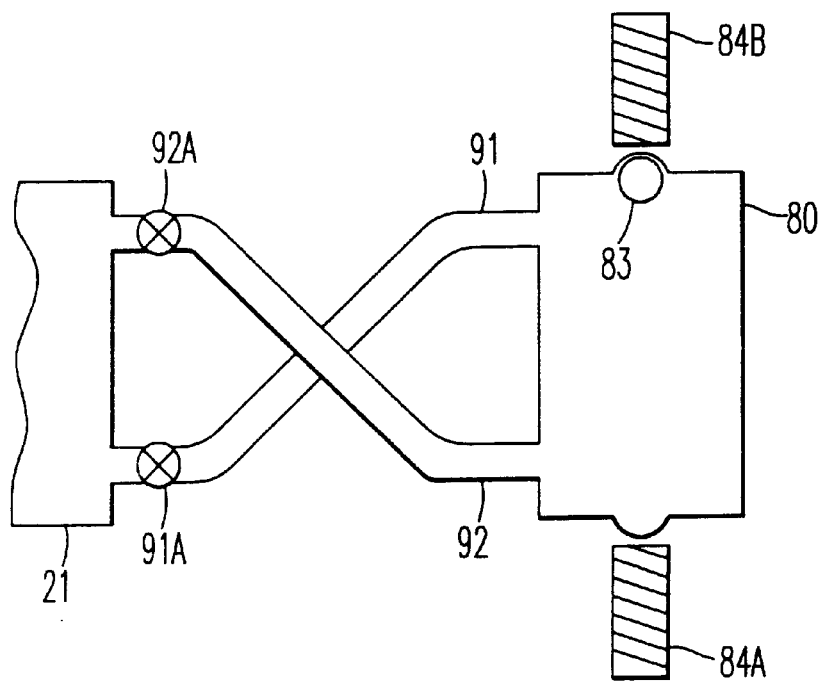

As shown in FIGS. 21(a) and 21(b), a pair of dents for accepting a steel ball 83 therein are respectively disposed at a bottom portion and a top portion of a developer density detecting box 80. A pair of electromagnets 84a, 84b are respectively disposed above and below the developer density detecting box 80 and are respectively adjacent to each of the dents and connect to the developer density detecting box 80. Both a developer supplying pipe 91 and a developer ejecting pipe 92 connect the developer tank 21 and the developer density detecting box 80. A pair of reversible pumps 91a and 92a are respectively disposed in the developer supplying pipe 91 and the developer ejecting pipe 92. Both of the reversible pumps 91a and 92a have functions of both supplying and ejecting liquid type developer 20 to and from the developer density detecting box 80, and these functions can be alternately utilized each time the developer density detecting box 80 is turned upside down, thereby changing liquid type developer 20 contained in the developer density detecting box 80 with another one contained in the developer tank 21. A swinging motor (not shown) is employed to swing the developer density detecting box 80 to be upside down.

When a preceding developer density detection is completed, a steel ball 83 staying in a dent formed on a bottom of a developer density detecting box 80 (hereinafter referred to as a bottom dent) is attracted by an electromagnet 84b disposed below the dent. Then, the developer density detecting box 80 swings to be upside down twisting both the developer supplying pipe 91 and the developer ejecting pipe 92 as shown in FIG. 21(b). Before a start of a next developer density detection of a liquid type developer 20, a fresh liquid type developer 20 is supplied by reversible pump 91a, which then acts as a developer supplying pump, through developer supplying pipe 91 from developer tank 21 which was used in a preceding developer density detection as a developer ejecting pipe for ejecting liquid type developer 20 from developer density detecting box 80 to the developer tank 21, and used liquid type developer 20 remaining in the developer density detecting box 80 is ejected by the reversible pump 92a, which then acts as a developer ejecting pump, through the developer ejecting pipe 92 which was used in a preceding detection as a developer supplying pipe for supplying liquid type developer 20 from the developer tank 21 to the developer density detecting box 80. This operation thereby changes a liquid type developer 20 to be detected.

After the liquid type developer 20 contained in a developer density detecting box 80 has been changed with new developer, a next developer density detection starts as described below. Namely, supplying of electricity to the electromagnet 84b is stopped to cause steel ball 83 to fall into a newly supplied liquid type developer 20 contained in developer density detecting box 80. A time at which the steel ball 83 starts falling into liquid type developer 20 contained in developer density detecting box 80 until it reaches a bottom thereof is measured by a timer or the like. Thereby, viscosity of the newly supplied liquid type developer 20 is calculated based upon the time period, for example. As explained in the earlier described embodiment, density is determined based upon viscosity referring to relations between viscosity of a liquid type developer and density thereof. By thus operating, density detection can be repeated as required.

Figure 22:
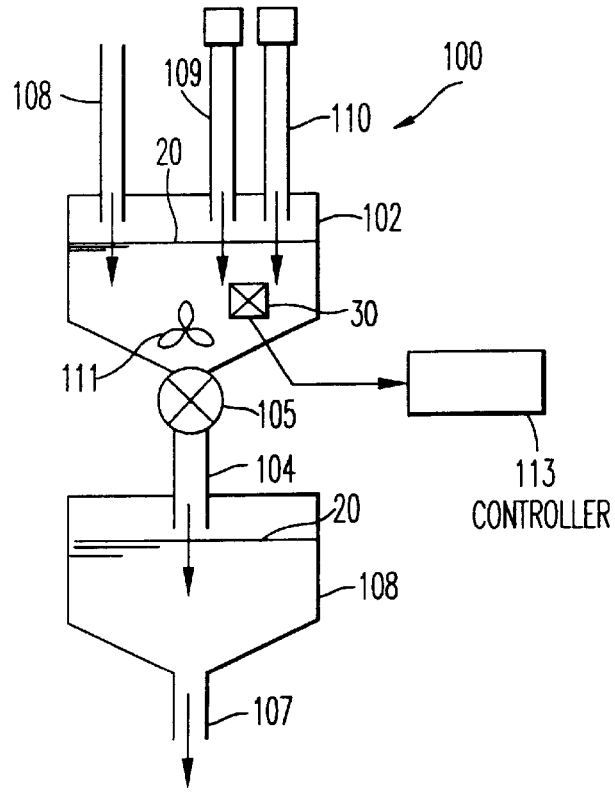
FIG. 22 is a schematic cross sectional view of a developer density control device of the present invention which employs a developer density detecting device for detecting density by measuring viscosity.
Figure 23:
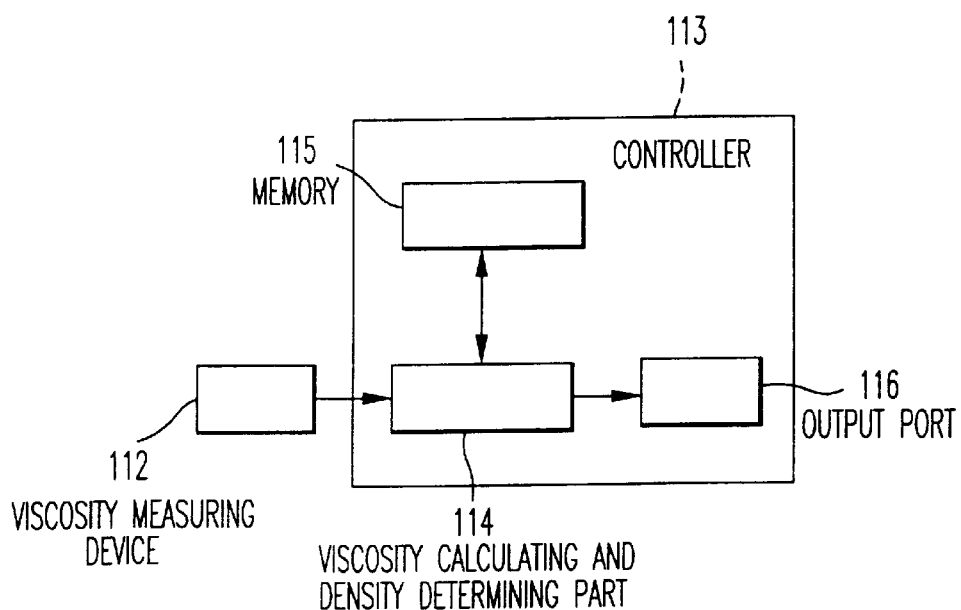
FIG. 23 is a block diagram of a controller.

Hereinafter, still another embodiment of the present invention is explained referring to FIG. 22. A developer density control device having an improved developer density detecting device for detecting density of a liquid type developer is illustrated in FIG. 22. A block diagram of the improved developer density detecting device for detecting density of a liquid type developer is illustrated in FIG. 23 in which developer density is detected by calculating viscosity obtained by measuring a torque of a motor for driving a member contacting a liquid type developer 20 as an object of density detection which is adopted to the developer density control device.

As shown in FIG. 22, a developer density control device 100 includes an upper tank 102 for storing a liquid type developer 20 therein, a developer collecting pipe 108 for collecting a reusable developer from a developer tank disposed at a developing station (not shown), a lighter developer adding pipe 109 for supplying a lighter developer to the upper tank 102, a darker developer adding pipe 110 for supplying a darker developer to the upper tank 102, a fan 111 for stirring liquid type developer 20 collected through the developer collecting pipe and a darker developer or a lighter developer selectively supplied to the upper tank 102, a viscosity measuring device 112 for measuring viscosity disposed in the upper tank 102, a lower tank 103 for tentatively storing a liquid type developer 20 having a predetermined density, a connecting pipe 104 for leading liquid type developer 20 from the upper tank 102 to the lower tank 103, a valve 105 for allowing or inhibiting passage of the liquid type developer from the upper tank 102, the valve 105 being disposed in the connecting pipe 104, and a developer leading pipe 107 for leading the liquid type developer 20 tentatively stored in the lower tank 103 to a developer tank disposed at a developer station (not shown).

The developer density control device further includes a controller or CPU 113 for controlling both a darker developer supplying device (not shown) and a lighter developer supplying device (not shown) to maintain a predetermined density of liquid type developer 20 contained in the upper tank 102 within a predetermined range by calculating viscosity and determining density of the liquid type developer 20. As shown in FIG. 23, the CPU 113 includes a memory 115 for storing information of relations between viscosity of liquid type developer and density thereof, a viscosity calculating and density determining part 114 and an output port 116 for outputting a control signal to either a darker developer supplying device (not shown) or a lighter developer supplying device (not shown).

Figure 24:
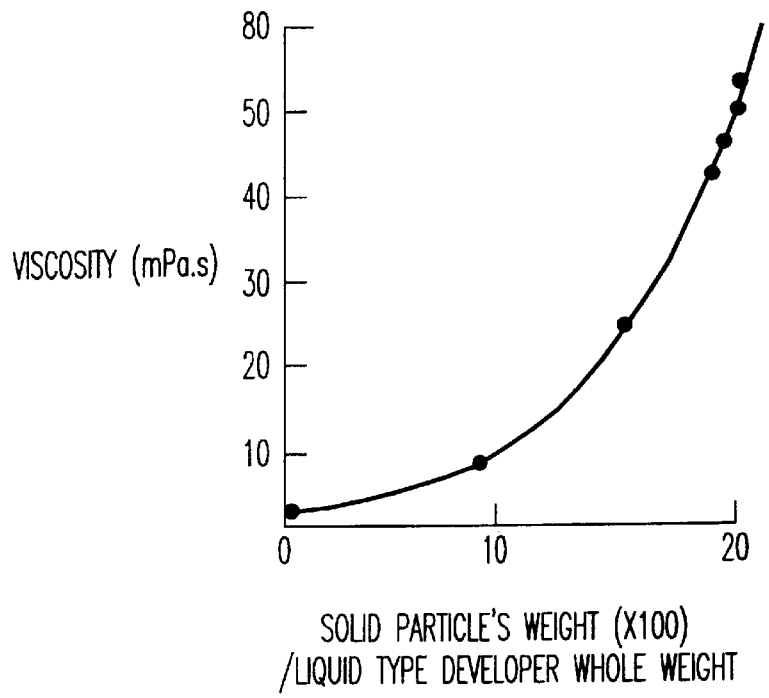
FIG. 24 is a graph showing relations between viscosity of a liquid type developer and density (a solid particle weight/a whole developer weight) thereof which is obtained experimentally.

Since liquid type developer 20 is composed of a liquid type carrier and solid particles of a pigment and a resin, etc., viscosity of the liquid type developer 20 is represented by a ratio between a weight of the solid particles and a whole weight of the liquid type developer 20. As shown in FIG. 24 and also described earlier, viscosity of the liquid type developer is related to the density thereof, namely, the darker or higher the density of the liquid type developer 20, the higher the viscosity of the liquid type developer 20. Therefore, if a look-up table (not shown) showing relations between viscosity of liquid type developer 20 and density thereof is stored in a memory 115 disposed in the CPU 113, density of the liquid type developer 20 can be determined by measuring viscosity of the liquid type developer 20 by the CPU 113 using the look-up table.

Hereinafter, an operation of the above described embodiment is explained in detail referring to FIGS. 22 and 23. A reusable liquid type developer 20 is collected among a liquid type developer used in a developing station and is supplied to an upper tank 102 through a collecting pipe 108 as shown by an arrow illustrated in FIG. 22, and then viscosity thereof is measured by a developer density detecting device 30. Density of the collected liquid type developer 20 collected is detected based upon viscosity referring to a table showing relations between viscosity of a liquid type developer and density thereof which is stored in the memory 115 in the CPU 113. The CPU 113 controls a darker developer supplying device (not shown) and/or a lighter developer supplying device (not shown) for respectively supplying either a darker developer or a lighter developer to the upper tank 102 to maintain a predetermined density of the liquid type developer 20 therein within a predetermined range in a manner as described below.

If density of a liquid type developer 20 is lighter than the predetermined range, a darker liquid type developer is supplied through the darker developer adding pipe 110 until the density thereof becomes within the predetermined range. On the other hand, if density of the liquid type developer 20 is darker than the predetermined range, a lighter liquid type developer is supplied through the lighter developer adding pipe 109 until the density thereof becomes within the predetermined range. Therefore, density of the liquid type developer 20 stored in the upper tank 102 is always kept within the predetermined range.

A valve 105 is controlled to open a connecting pipe 104 to supply the liquid type developer 20 having predetermined density to the lower tank 103 after the liquid type developer 20 stored in the upper tank 102 becomes within predetermined density and to shut the connecting pipe 104 when a predetermined volume of liquid type developer 20 has passed through the connecting pipe 104. The liquid type developer 20 stored in the lower tank 103 is supplied to a developer tank disposed in a developing station (not shown) for developing a latent image formed on an image carrier (not shown). Thereby, the liquid type developer having the predetermined density is continuously supplied to the developer tank disposed in a developing station of an image forming apparatus.

Since relations between viscosity of a liquid type developer and density thereof varies depending upon temperature, it is preferable to keep a temperature of liquid type developer 20 stored in the upper tank 102 within a predetermined range when detecting density thereof Therefore, a heating device for heating a liquid type developer 20 and a controller for controlling the temperature thereof within a predetermined range can be adopted to the above described embodiment.

Further, since relations between viscosity of a liquid type developer and density thereof varies depending upon temperature, it is preferable to use a look-up table representing relations between viscosity of liquid type developer 20 and density thereof for each of temperatures.

Hereinafter, still another embodiment of the present invention is explained referring to FIGS. 25, 26 and 27.

Figure 25:
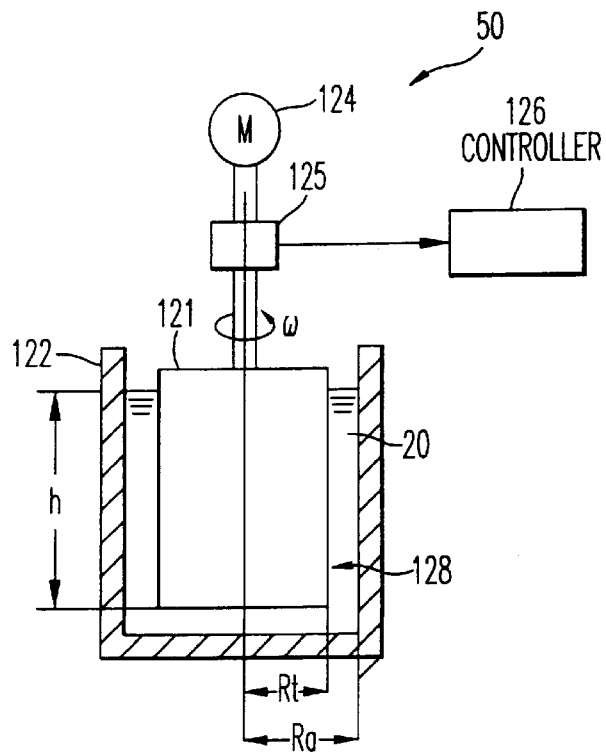
FIG. 25 is a cross sectional view of still another embodiment of the present invention, in which developer density is detected based upon viscosity by measuring a torque of a motor for driving a member contacting a liquid type developer as an object of density detection.

An improved developer density detecting device 50 which is adopted to the developer density control device 100 as shown in FIG. 24 is illustrated in FIG. 25 in which density of a liquid type developer is detected by measuring a torque of a motor for rotating a member contacting to and sinking in a liquid type developer 20 as an object of density detection.

As shown in FIG. 25, a developer density detecting device 50 for detecting density of a liquid type developer 20 includes an inner cylinder 121 and an outer cylinder 122 which are coaxially disposed, a motor for rotating the inner cylinder 121 with a predetermined rotational angle and a controller or CPU 126 including a viscosity calculating part 127 for calculating viscosity of a liquid type developer 20. A liquid type developer 20 as an object of density detection is stored between the inner cylinder 121 and the outer cylinder 122. A block diagram of the CPU 126 is illustrated in FIG. 26.

Figure 26:
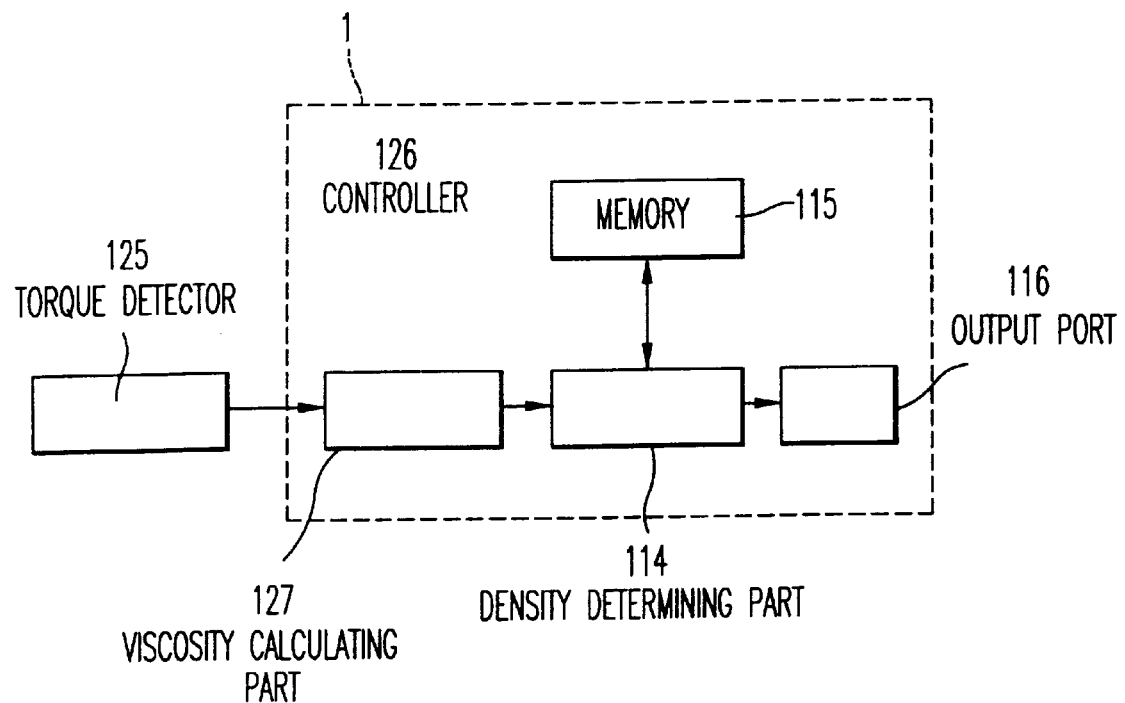
FIG. 26 is a block diagram of a controller for measuring viscosity and determining density of a liquid type developer.

As shown in FIG. 26, the CPU 126 includes a viscosity calculating part 127 for to calculating viscosity of the liquid type developer 20 based on a torque measured by a torque detector 125, a memory 115 for storing information of relations between viscosity of a liquid type developer and density thereof, a density determining part 114 for determining density of a liquid type developer based upon the viscosity thereof referring to relations between viscosity of a liquid type developer and density thereof stored in the memory 115, and an output port 116 for outputting a control signal to either a darker developer supplying device (not shown) or a lighter developer supplying device (not shown).

Hereinafter, a viscosity measuring operation in which viscosity of a liquid type developer 20 is measured based upon a torque of a motor is explained.

Generally, fluid is classified into three types, namely a NEWTONIAN fluid, a NON-NEWTONIAN fluid and a NON-NEWTONIAN fluid having a yield point and, any way, viscosity $\mu$ of each of the fluids is generally obtained by dividing (T) by (D), wherein (D) represents a shear rate and (T) represents a shear stress thereof. Relations between a shear rate (D) and a sheer stress (T) are illustrated in FIG. 27.

Since a liquid type developer 20 belongs to one of the fluids described above, if both of a shear rate (D) and a shear stress (T) thereof are measured, viscosity of a liquid type developer is accordingly obtained and density thereof is determined based upon the viscosity referring to relations between viscosity of a liquid type developer and density thereof as shown in FIG. 24. To measure viscosity of a liquid type developer 20 in a manner as described above, the below described operation is executed. A liquid type developer 20 is supplied into a space 128 formed between an inner cylinder 121 and an outer cylinder 122, and the inner cylinder 121 is rotated by motor 124 with a predetermined angular velocity. A torque of the motor 124 is detected by a torque detector 125 when the inner cylinder 121 is rotated in a state of contacting the liquid type developer 20, and the torque detector 125 generates a signal indicative of a torque and sends it to a viscosity calculating part 127 in CPU 126. The viscosity calculating part 127 measures viscosity based upon the torque of the motor 124 in a manner as described below.

If a radius of the inner cylinder 121 is (Ri), a radius of the outer cylinder 122 is (Ra), a height of a surface of the liquid type developer 20 stored in a space 128 formed between the inner cylinder 121 and the outer cylinder 122 from a bottom of the inner cylinder 121 is (h), an angular velocity of the inner cylinder 121 is ((a) and torque detected by torque detector 125 is (M), both a shear rate (Di) of a liquid type developer 20 and shear stress (Ti) thereof are given as below described formulas (4) and (5).

$$Di = 2\omega Ra^2/(Ra^2 - Ri^2) \quad (4),$$

$$Ti = M/2\pi h Ri^2 \quad (5)$$

The viscosity calculating part 127 measures viscosity $\mu$ of the liquid type developer 20 by dividing Ti by Di, and sends the viscosity information to density determining part 114 in the CPU 126. The density determining part 114 determines density of the liquid type developer 20 based upon the viscosity referring to relations between viscosity of a liquid type developer and density thereof as shown in FIG. 24 which is stored in memory 115 of the CPU 126.

The above described embodiment of the invention is especially suitable for detecting a liquid type developer having high density or high viscosity, since a torque of a motor for rotating a cylinder contacting such a liquid type developer is relatively large, thereby precise calculation by a viscosity calculating part in CPU 126 is obtained.

A same result may be obtained if the outer cylinder 122 is rotated and a torque of a motor for rotating the outer cylinder 122 is measured while securing an inner cylinder 121, instead of rotating an inner cylinder 121 as described above. Further, a same result may also be obtained if a torque on a secured member, the outer cylinder 122 shown in FIG. 25 for example, is measured, instead of measuring a torque of a motor for rotating a member, the inner cylinder 121 shown in FIG. 25 for example.

Hereinafter, still another embodiment of the present invention is explained referring to FIG. 28.

Figure 28:
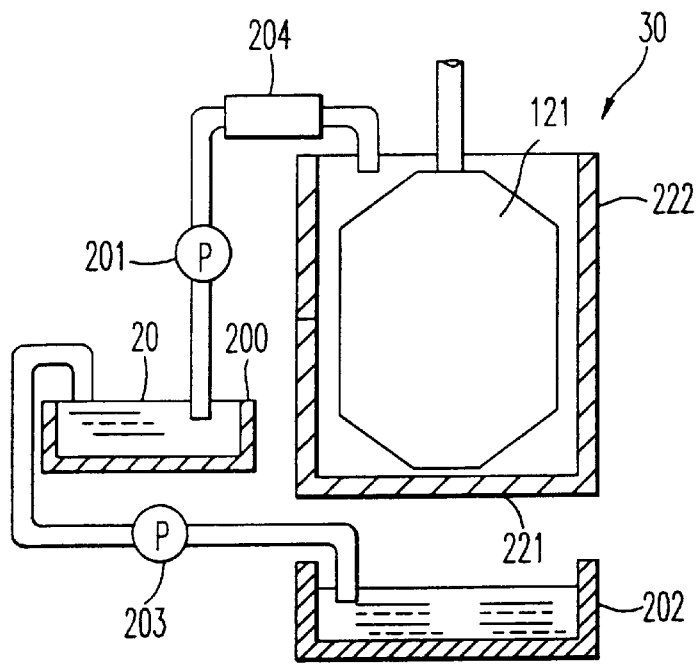
FIG. 28 is a schematic cross sectional view of still another embodiment of the present invention in which density of a liquid type developer is detected based upon viscosity by measuring a torque of a motor for rotating a cylinder contacting a liquid type developer as an object of density detection.

A developing device for developing a latent image formed on an image carrier (not shown) with a liquid type developer is illustrated in FIG. 28 which employs an improved developer density detecting device.

As shown in FIG. 28, the developing device includes a developing tank 200 for storing a liquid type developer 20 and developing a latent image formed on an image carrier (not shown), a pump 201 for sending the liquid type developer stored in the developing tank 200, a heating element 204 for heating liquid type developer passing through the heating element 204 and a developer density detecting device 30. The developer density detecting device 30 includes an outer cylinder 222 for containing liquid type developer 20 as an object of density detection, a plurality of ejecting holes 221 for ejecting the liquid type developer formed at a bottom of the outer cylinder 222, a developer receiving vessel 202 for receiving the liquid type developer 20 ejected from the outer cylinder 222 through the ejecting holes 221 disposed below the outer cylinder 222, a developer circulating pipe for circulating the liquid type developer from the developer receiving vessel 202 to the developing tank 200 and a pump 203 for sending the liquid type developer 20 from the developer receiving vessel 202 to the developing tank 200. Thereby, a liquid type developer 20 is circulated through the above described devices.

Viscosity of the liquid type developer 20 contained in the space formed between the inner cylinder 121 and the outer cylinder 222 is detected by measuring a torque of a motor (not shown) for rotating the inner cylinder 121 while ejecting a liquid type developer 20 through the ejecting holes 221. Detection of density, however, is not influenced by flowing stress of the liquid type developer 20 ejected through the ejecting holes 221, since only gravity is put onto the liquid type developer 20 as an object of density detection stored in the space between the inner cylinder 121 and the outer cylinder 222, thereby obtaining a precise detection of density of liquid type developer 20.

Since viscosity of the liquid type developer 20, and accordingly density thereof, changes depending upon temperature, a heating element 204 for heating the liquid type developer 20 is connected to a developer circulating pipe. A sensor (not shown) for sensing a temperature of the liquid type developer 20 and a temperature controller (not shown) can be employed in FIG. 28 for controlling the heater element 204 to maintain a temperature of the liquid type developer 20 within a predetermined range. Therefore, a temperature of the liquid type developer 20 is always kept within a predetermined range, and accordingly a stable density detection of the liquid typed developer 20 is obtained by the above described embodiment regardless of a change in temperature.

Hereinafter, still another embodiment of the present invention is explained referring to FIG. 29. An improved developer density detecting device of the present invention is illustrated in FIG. 29.

Figure 29:
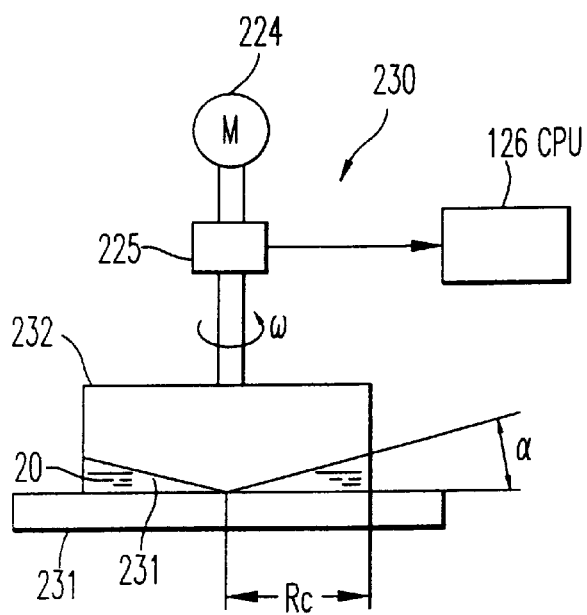
FIG. 29 is a schematic cross sectional view of still another embodiment of the present invention in which density of a liquid type developer is detected based upon viscosity by measuring a torque of a cylinder having a cone shape which contacts a liquid type developer as an object of density detection.

As shown in FIG. 29, the improved density detecting device 230 includes a plain disc 231 disposed in a density detecting box (not shown), a cone 232 disposed also in the density detecting box in a state that a peak of which contacts a center of an upper surface of the plain disc 231, a driving motor 224 for rotating the cone 232 with a predetermined angular velocity ($\omega$) via an axis thereof and a torque detector 225 for detecting torque of the driving motor 224 when rotating the cone 232.

In such a device, a torque is detected by the torque detector 225 in a manner as described below. Firstly, liquid type developer 20 is supplied into the density detecting box (not shown) to enter into a space 233 formed between the plain disc 231 and the cone 232 as shown in FIG. 29. The cone 232 is rotated in a predetermined direction by driving motor 224 with a predetermined angular velocity ($\omega$) in a state that the cone 232 contacts the liquid type developer 20 as an object of density detection stored in the space formed between the plain disc 231 and the cone 232, while the plain disc 231 is secured to the developer density detecting box (not shown).

When the cone 232 is rotated by the motor 224, a torque of the motor 224 is detected by the torque detector 225 and the torque detector 225 generates and sends a signal indicative of a torque to a viscosity calculating part in CPU 126. Generally, if an angle between the plain disc 231 and the cone 232 is ($\alpha$), a radius of the cone 232 is (Dc) and a torque measured by the torque detector 225 is (M), both a shear rate (Dc) of the liquid type developer 20 and a shear stress (Tc) thereof are obtained as below described formulas (6) and (7).

$$Dc = \omega / \tan \alpha \quad (6)$$

$$Tc = 3M / 2\pi Rc^3 \quad (7)$$

The viscosity calculating part in the CPU 126 calculates Dc and Tc based upon the torque M detected by the torque detector 225 to calculate viscosity $\mu$ of the liquid type developer 20 by dividing Tc by Dc. A density determining part determines density of the liquid type developer 20 based upon the viscosity calculated by the viscosity calculating part referring to information of relations between viscosity of a liquid type developer and density thereof which is stored in a memory of the CPU 126.

A same result will be obtained if the plain disc 231 is rotated and a torque of the motor 224 for rotating the plain disc 231 is measured while the cone 232 is secured to the developer density detecting box (not shown), instead of rotating the cone 232 and measuring a torque of motor 224 for rotating the cone 232 as described above.

Further, a same result will also be obtained if a torque on a fixed member, the plain disc 231 illustrated in FIG. 29 for example, is measured for obtaining viscosity of a liquid type developer 20 stored in developer density detecting box (not shown) instead of measuring a torque of a rotating member.

Further, since viscosity of a liquid type developer changes depending upon temperature, a temperature controller (not shown) can be employed to maintain a temperature of the liquid type developer within a predetermined range to thereby obtain a stable detection of density regardless of a change in temperature.

Further, if an angular velocity (a) of a driving motor 224 for rotating an inner cylinder 221 as shown in FIG. 25 and the cone 232 as shown in FIG. 29 are selected to be almost the same as a shear rate of the liquid type developer 20, a more precise density detection of the liquid type developer is obtained.

Figure 27:
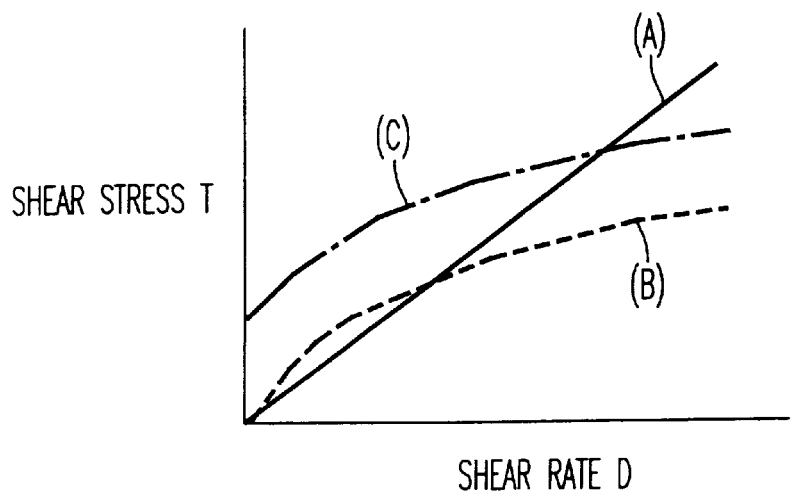
FIG. 27 is a graph showing relations between a shear stress (T) and a shear rate (D) of a fluid.

Further, if a liquid type developer 20 is a NON-NEWTONIAN fluid having a yield point on a graph showing a relation between a shear rate (D) and a shear stress (T) of a fluid, and accordingly a curvature (c) representing relations between a shear rate (D) and shear stress (T) of the liquid type developer is not linear as shown in FIG. 27, viscosity of such a liquid type developer 20 is precisely detected in the above described embodiment.

Figure 30:
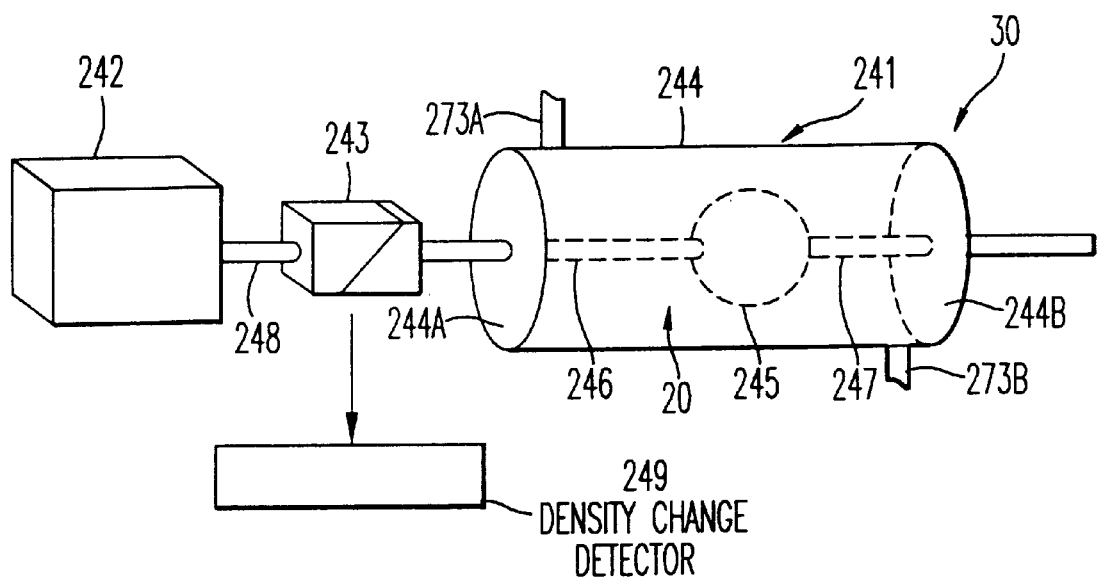
FIG. 30 is a cross sectional view of still another embodiment of the present invention in which density is detected by measuring a resisting force of a liquid type developer as an object of density detection when the liquid type developer is moved by a steel ball.

Further, if density of a liquid type developer 20 is detected a plurality of times by changing an angular velocity ($\omega$) of motor 224 for rotating either inner cylinder 221 shown in FIG. 25 or cone 232 shown in FIG. 30, density is more precisely obtained by the above described embodiments even if a fluid does not belong to a NEWTONIAN fluid, namely a NON-NEWTONIAN fluid or a NON-NEWTONIAN fluid having a yield point.

Hereinafter, still another embodiment of the present invention is explained referring to FIG. 30. An improved developer density detecting device 30 is illustrated in FIG. 30 in which a change in density of a liquid type developer 20 is measured and the density thereof is controlled to be maintained within a predetermined range in response to a change in density.

As shown in FIG. 30, an improved developer density detecting device 30 includes a piston 241 including a cylinder 244 for storing a liquid type developer 20 as an object of density detection therein and a steel ball 245 for moving in cylinder 244, the steel ball 245 having a predetermined size and being mounted on shafts 246 and 247 respectively protruding from the cylinder, a driving unit 242 for reciprocally pushing and pulling the steel ball 245, a connecting shaft 248 for transmitting a pushing and a pulling force caused by the driving unit 242, a piezoelectric member 243 for detecting a resisting force of the liquid type developer contained in the piston 241 against the steel ball 245 when the steel ball 245 is pushed or pulled by the driving unit 242 and which generates a voltage signal indicative of a resisting force, a developer supplying pipe 273a for supplying liquid type developer 20 as an object of density detection into the cylinder 244 of the piston 241 connected to the cylinder 244, and a developer ejecting pipe 273b for ejecting the liquid type developer 20 from the cylinder 244 after density detection thereof is completed and which is connected to the cylinder 244.

The liquid type developer 20 in the cylinder 244 is changed with new liquid type developer 20 before density detection starts by ejecting the liquid type developer through the developer ejecting pipe 273b and supplying new liquid type developer through the developer supplying pipe 273a. The steel ball 245 is firmly supported by the pair of shafts 246 and 247 respectively elongated in a direction parallel to an axis of the cylinder 244. The shaft 246 is movably supported by a bearing (not shown) mounted on a side wall 244a near the piezoelectric member 243 of the cylinder 244 and which protrudes from the side wall 244a and connects with the piezoelectric member 243. The other shaft 247 mounting the steel ball 245 thereon is also movably supported by a bearing (not shown) mounted on another side wall 244b of the cylinder 244 and protruding therefrom. The steel ball 245 thus supported by both the shafts 246 and 247 freely moves in a direction parallel to an axis of the cylinder 244 in contact with the liquid type developer 20 contained in the cylinder 244 when pushed or pulled by the dp sing unit 242.

The driving unit 242 includes a motor and a gear involving a rack and a pinion or a linear motor type actuator. The piezoelectric member 243 is connected by both the shafts 246 and 248 respectively mounting the steel ball 245, thereby receiving a resisting force of the liquid type developer 20 contained in the cylinder 244 against the steel ball 245 via the shaft 246 and generating a voltage corresponding to the resisting force, and sending a voltage signal indicative of the resisting force of the liquid type developer 20 to a developer density change detector 249 included in CPU 113 shown in FIG. 22 when the driving unit pushes or pulls the steel ball 245 in contact with the liquid type developer 20 contained in the cylinder 244 via the shaft 248.

The developer density change detector 249 calculates a change in density based upon the voltage signal generated by the piezoelectric member 243 referring to a predetermined reference voltage which corresponds to a normal density.

In such a detection, the larger the resisting force D of the liquid type developer 20, the higher the density of the liquid type developer.

Hereinafter, an operation of density detection of a liquid type developer 20 by the above described device is explained. Before a start of density detection of a liquid type developer 20, liquid type developer 20 remaining in a cylinder 244 of piston 241 of developer density detecting device 30 is ejected through developer ejecting pipe 273b and new developer is supplied through developer supplying pipe 273a.

Density detection of liquid type developer 20 starts when the steel ball 245 is moved to a position near the side wall 244a of cylinder 244, which is an initial position for density detection utilizing the steel ball 245, and when a predetermined time in which the liquid type developer 20 filled into the cylinder 244 stops it's movement in the cylinder 244 has elapsed. Then, driving unit 242 starts driving to pu-n the steel ball 245 in a direction parallel to an axis of the cylinder 244 against the other side wall 244b of the cylinder 244. A voltage signal generated by the piezoelectric member 243 is sent to a density change detector 249 when a moving velocity of the steel ball 245 becomes constant since a moving velocity of liquid type developer 20 only becomes stable shortly after a start of moving. A moving velocity of the steel ball 245 is measured by a pulse encoder (not shown) which generates pulses corresponding to a rotational frequency of the driving motor disposed in the driving unit 242, for example.

The voltage generated by the piezoelectric member 243 corresponds to both a driving force of the driving motor in the driving unit 242, which is caused when pushing the steel ball 245 with a speed (U), and a resisting force D of the liquid type developer 20 contained in the cylinder 244 against the steel ball 245, which is caused when pushed by the steel ball 245. The voltage signal is sent to the density change detector 249, thereby detecting a change in density of liquid type developer 20 by comparing the voltage signal generated by the piezoelectric member 243 with a predetermined reference voltage corresponding to a normal density.

Density of the liquid type developer 20 for use in a developing device is controlled to maintain a density of liquid type developer 20 within a predetermined range based upon a change in density detected by the density change detector 249. For example, if the piezoelectric element 249 generates a larger voltage than a predetermined reference voltage which corresponds to a normal density of a liquid type developer, and accordingly the density change detector 249 detects a change in density as darker than a normal density, a lighter developer is added to the liquid type developer contained in the developing device (not shown) disposed at the developing station (not shown).

The above described density change detection is repeated each time liquid type developer 20 contained in the cylinder 244 is changed with new developer.

Hereinafter still another embodiment of the present invention is explained referring to FIG. 31.

Figure 31:
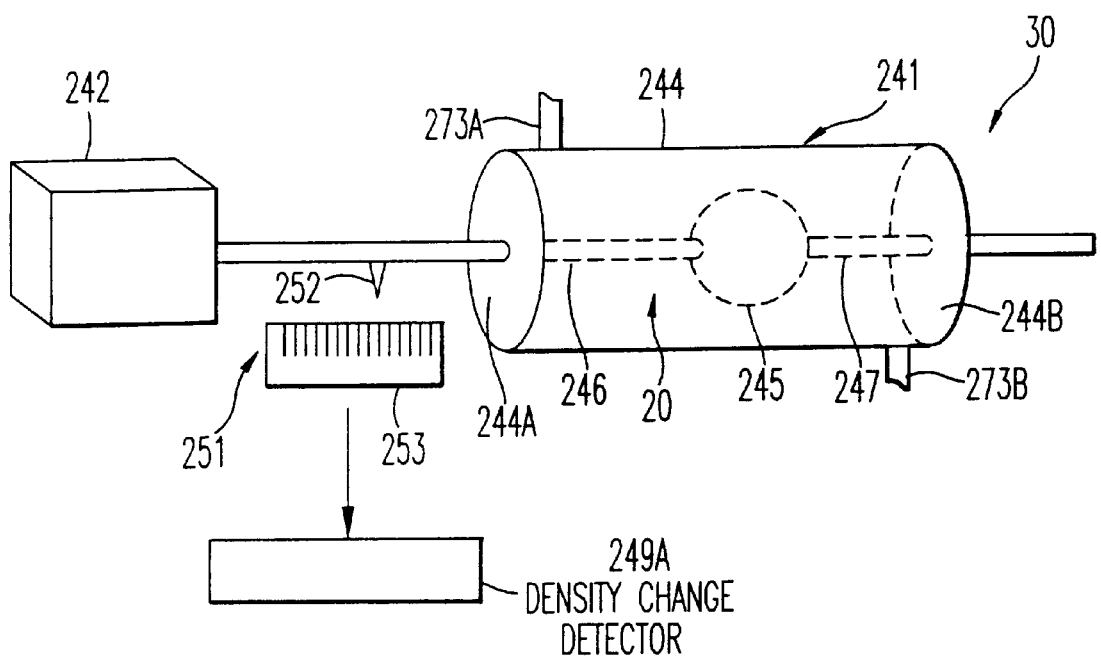
FIG. 31 is a cross sectional view of still another embodiment of the present invention in which density is detected by measuring viscosity by detecting a moving distance of a steel ball sinking in a liquid type developer as an object of density detection, when the steel ball is pushed with a predetermined force.

A further improved density change detecting device is illustrated in FIG. 31. As shown in FIG. 31, a density detecting device 30 includes almost the same device as in the above described embodiment shown in FIG. 30. This embodiment, however, includes a moving distance measuring device 251 for measuring a moving distance of steel ball 245 moving in contact with liquid type developer 20 contained in cylinder 244, instead of using the piezoelectric member 243 shown in FIG. 30, and which includes an indicator 252 secured to a connecting shaft 246 for transmitting a pushing or a pulling force of steel ball 245 and a scale 253 disposed adjacent to the indicator 252.

Hereinafter, an operation of density detection by using such a device is explained.

Density detection of a liquid type developer 20 starts when the steel ball 245 in the cylinder 244 is positioned where indicator 252 indicates a zero point on scale 253, and when a predetermined time in which the liquid type developer 20 newly supplied into the cylinder 244 stops it's movement has elapsed. Then, a driving unit 242 pushes the steel ball 245 via a shaft 246 with a predetermined constant pushing force toward the other wall 244b of the cylinder 244 in parallel to an axis of the cylinder 244.

A moving distance during a predetermined time period of the indicator 252 is measured, and accordingly the steel ball 245 is automatically measured and a signal indicative of the moving distance during the predetermined time period is sent to density change detector 249a. A moving distance of steel ball 245 moving in liquid type developer 20 contained in cylinder 244 during the predetermined time depends on density of the liquid type developer 20 contained in the cylinder 244 if the steel ball 245 is pushed under a predetermined force by the driving unit 242.

Therefore, since the moving distance of steel ball 245 is related to density of the liquid type developer 20, the higher the density of the liquid type developer 20, the shorter the moving distance of the steel ball 245. A density change detector 249a detects change in density based on the moving distance of the steel ball 245 on the scale 253, by referring to a reference distance which corresponds to a normal density. The above described density detection is repeated each time after the liquid type developer 20 contained in the cylinder 244 has been changed with new developer.

A moving distance on scale 253 of steel ball 245 can be sensed by a conventional sliding resister which generates a voltage in proportion to a moving distance on the scale 253. Thus, viscosity is measured based on the voltage detected with a reference voltage which corresponds to a normal density. Thus, a controller adds a darker developer to a liquid type developer 20 stored in a developer tank (not shown) if the density change detector detects that a liquid type developer 20 is lighter.

A same result is obtained if a time is measured instead of measuring a moving distance in which steel ball 245 moves a predetermined distance in contact with liquid type developer 20 contained in cylinder 244 when pushed under a predetermined force by the driving unit 242.

Further, instead of measuring a moving distance of steel ball 245 for detecting a change in density of liquid type developer 20 contained in cylinder 244, a technology of detecting a pressure or velocity of liquid type developer 20 which is moved by steel ball 245 can be used and a same result can be obtained.

Hereinafter, still another embodiment of the present invention is explained referring to FIG. 32. An improved developer density detecting device 30 is illustrated in FIG. 32 in which pressure or velocity of a liquid type developer 20 contained in cylinder 244 is measured when the same is moved by a steel ball 245 moving in the cylinder 244 of a piston 260.

Figure 32:
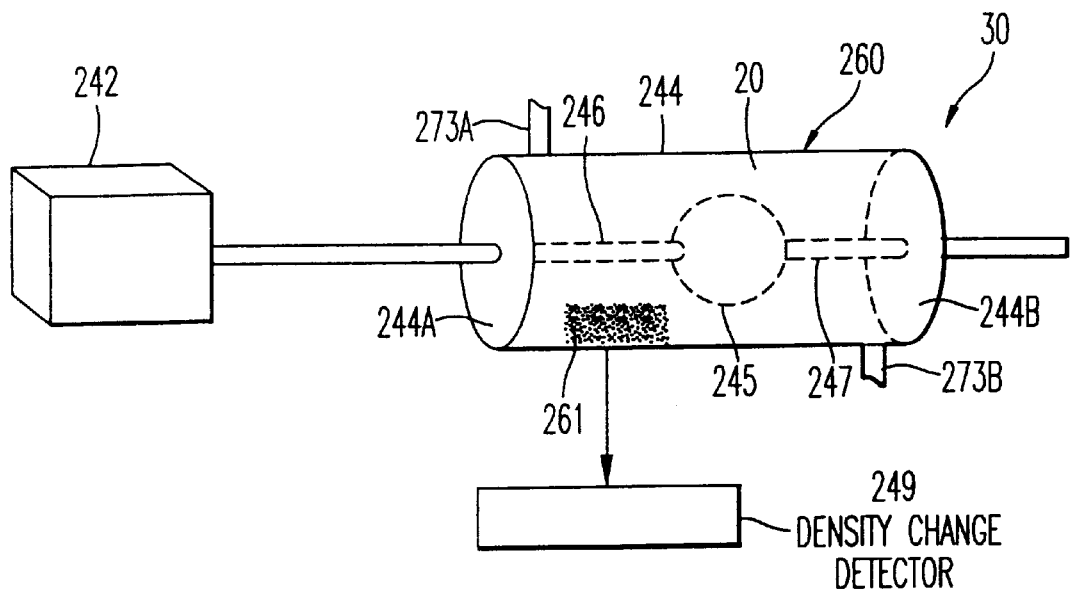
FIG. 32 is a cross sectional view of still another embodiment of the present invention in which density is detected bared upon viscosity by measuring pressure of a liquid type developer when a steel bill sinking in the liquid type developer is moved horizontally.

As shown in FIG. 32, a density detecting device 30 includes a piston 260 including a cylinder 244 and a steel ball 245 mounted on shafts 246 and 247 installed in the cylinder 244 and a driving unit 242 for moving the steel ball 245 via shaft 246. A flowing detector 261 is disposed in the cylinder 244 for detecting pressure or velocity of liquid type developer 20, which is produced by the steel ball 245 when moving through the liquid type developer 20. The flowing detector 261 is disposed at a position where the flowing detector 261 does not obstruct movement of the steel ball 245 and is electrically connected to a density change detector 249b.

Due to large variations in a scale or a wave shape of a signal generated by flowing detector 261 corresponding to a position where the flowing detector 261 is positioned, a shape of a cylinder 244, a scale of the steel ball 245 and so on, flowing detector 261 is designed to have a high responsibility against a small density change.

Hereinafter, an operation of density change detection of a liquid type developer by the above described device is explained. Steel ball 245 in cylinder 244 of piston 260 is firstly positioned near a side wall 244a of the cylinder 244. A liquid type developer 20 as an object of density detection is supplied into the cylinder 244 at this moment.

After the liquid type developer 20 supplied into the cylinder 244 and all of the liquid type developer supplied into the cylinder 244 has stopped it's movement, a driving unit 242 is activated to push the steel ball 245 in a direction parallel to an axis of the cylinder 244 toward another side wall 244b of the cylinder 244 with a predetermined speed. The steel ball 245 causes a flow of the liquid type developer 20 contained in the cylinder 244 and a flowing speed thereof or pressure of the liquid type developer 20 is deter ed by the flowing detector 261.

A flowing speed or pressure of the liquid type developer 20 varies depending upon density of the liquid type developer 20. Therefore, the density change detector 249b calculates change in density of the liquid type developer 20 contained in the cylinder 244 based upon a signal generated and output by flowing detector 261 referring to a predetermined reference velocity or pressure which respectively corresponds to a normal density. Density of a liquid type developer 20 is maintained within a predetermined range in response to detecting a result of density change detection.

Hereinafter, still another embodiment of the present invention is explained referring to FIG. 33. An improved developer density detecting device 30 is illustrated in FIG. 33 in which a change in density is detected by measuring a change in electricity of a motor for driving a fan contacting a liquid type developer 20 as an object of density detection.

Figure 33:
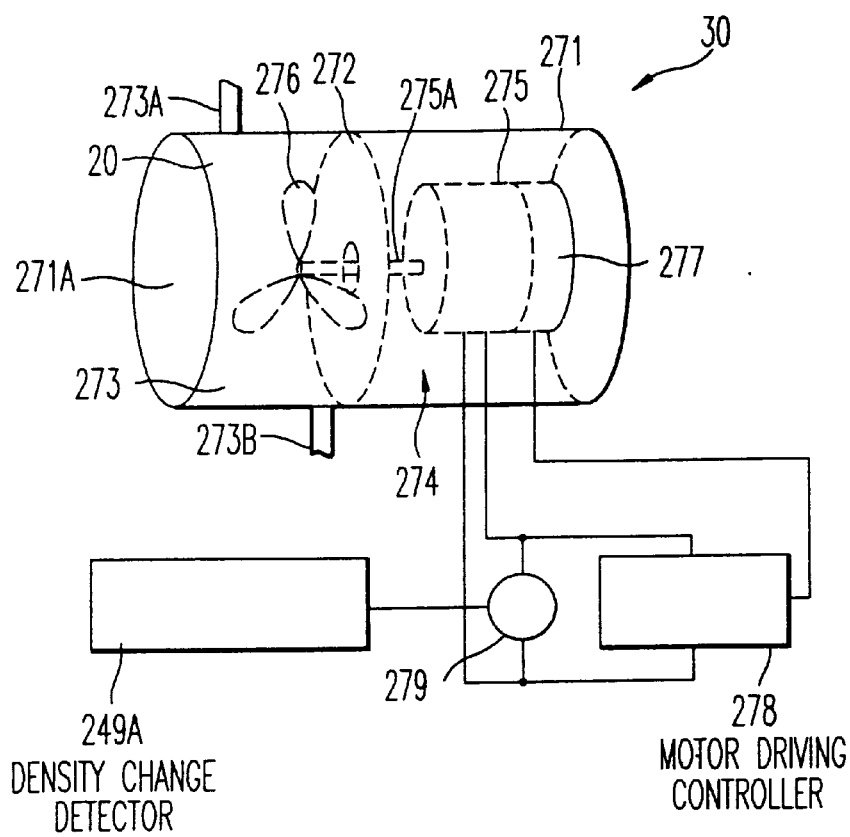
FIG. 33 is a cross sectional view of still another embodiment of the present invention in which density is detected by measuring a load on a motor for rotating a fan sinking in liquid type developer as an object of density detection when the fan is rotated by the motor.

As shown FIG. 33, a density detecting device 30 includes a cylindrical measuring case 271 for storing a liquid type developer 20 as an object of density detection divided into two areas 273 and 274 by a partition 272, a fan 276 for stirring the liquid type developer contained in the area 273, a DC motor 275 for driving fan 276 disposed in the area 274 and having a shaft 275a supported by a bearing mounted on the partition 272 (not shown) and which penetrates the partition 272 and protrudes into the area 273 to connect with the fan 276, a motor driving controller 278 for controlling the motor 275, an encoder 277 for generating pulses in accordance with a rotation of the DC motor 275 which is coaxially disposed with the motor 275, and an electricity detector 279 for detecting an electricity of the DC motor 275.

The developer density detecting device further includes a developer supplying pipe 273a for supplying a liquid type developer 20 as an object of density detection into the area 273 and a developer ejecting pipe 273b for ejecting liquid type developer 20 contained in the area 273 after density detection thereof is completed.

The motor driving controller 278 includes an electricity or voltage detector 279 for detecting an electricity or a voltage respectively supplied to the DC motor 275 from a power source and for generating a signal indicative of the electricity or a voltage, and a density change detector 249a for detecting a change in density of liquid type developer 20 based on the signal indicative of electricity or voltage generated by the electricity or voltage detector 279 referring to a reference electricity or voltage which corresponds to a normal density.

Hereinafter, an operation of density detection of a liquid type developer 20 in the above described device is explained below.

A liquid type developer 20 contained in the area 273 is changed before density detection starts. When a new liquid type developer 20 as an object of density detection is supplied into the area 273, the area 273 is mechanically sealed not to receive any influence from outside thereof. Electricity is supplied from an electrical power source to a DC motor 275 to rotate a fan 276 contacting the liquid type developer 20 under control of a motor driving controller 278. The motor driving controller 278 controls the DC motor 275 to rotate with a predetermined rotational frequency by detecting change in pulse counts per second which is generated by the encoder. Accordingly the fan 276 is also controlled to rotate with a predetermined rotational frequency.

When a certain time has elapsed after the DC motor 275 starts rotating in which a rotation of the fan 276 becomes stable, the developer density detecting device starts detecting density of the liquid type developer, since the rotation of the fan 276 is unstable shortly after the start of rotating.

If the DC motor 275 and accordingly fan 276, are controlled to maintain a predetermined rotational velocity by the motor driving controller 278, electricity to be supplied to the DC motor 275 varies depending upon density of the liquid type developer 20 stirred by the fan 276 driven by the DC motor 275, since a change in density is in proportion to a change in electricity. A density change detector 249a therefore calculates a change in density of liquid type developer 20 by detecting a change in electricity supplied to the DC motor 275 referring to a predetermined reference electricity which corresponds a normal viscosity.

Instead of using both the developer supplying pipe 273a and the developer ejecting pipe 273b for changing liquid type developer 20 as an object of density detection, a side wall 271a can be designed to selectively open or shut so as to lead a liquid type developer 20 into the area 273 and to eject thereof through the side wall 271a when the same is open.

Hereinafter, a slightly modified embodiment is described in FIG. 34.

If a predetermined electricity is continuously supplied to the DC motor 275 from the motor driving controller 278, a rotational frequency of both the fan 276 and the DC motor 275 changes depending upon density of the liquid type developer 20 contained in area 273. Since a rotational frequency thereof is in proportion to or related to density of the liquid type developer 20, the density thereof can be detected by measuring rotational frequency of the DC motor 275 with the encoder 277 by counting pluses while keeping an electricity supplied thereto in a predetermined amount.

Further, if a time at which shaft 275a of DC motor 275 comes to rotate within a predetermined rotational frequency from a start thereof is detected, since density is related to this time, the density of the liquid type developer 20 contained in the area 273 can also be measured referring to a reference time which corresponds to a normal density.

Instead of measuring a change in electricity of DC motor 275 as described above, a change in density can be measured by detecting a flowing velocity of the liquid type developer 20 or pressure thereof since both flowing velocity of the liquid type developer 20 and pressure thereof are respectively related to density thereof.

Figure 34:
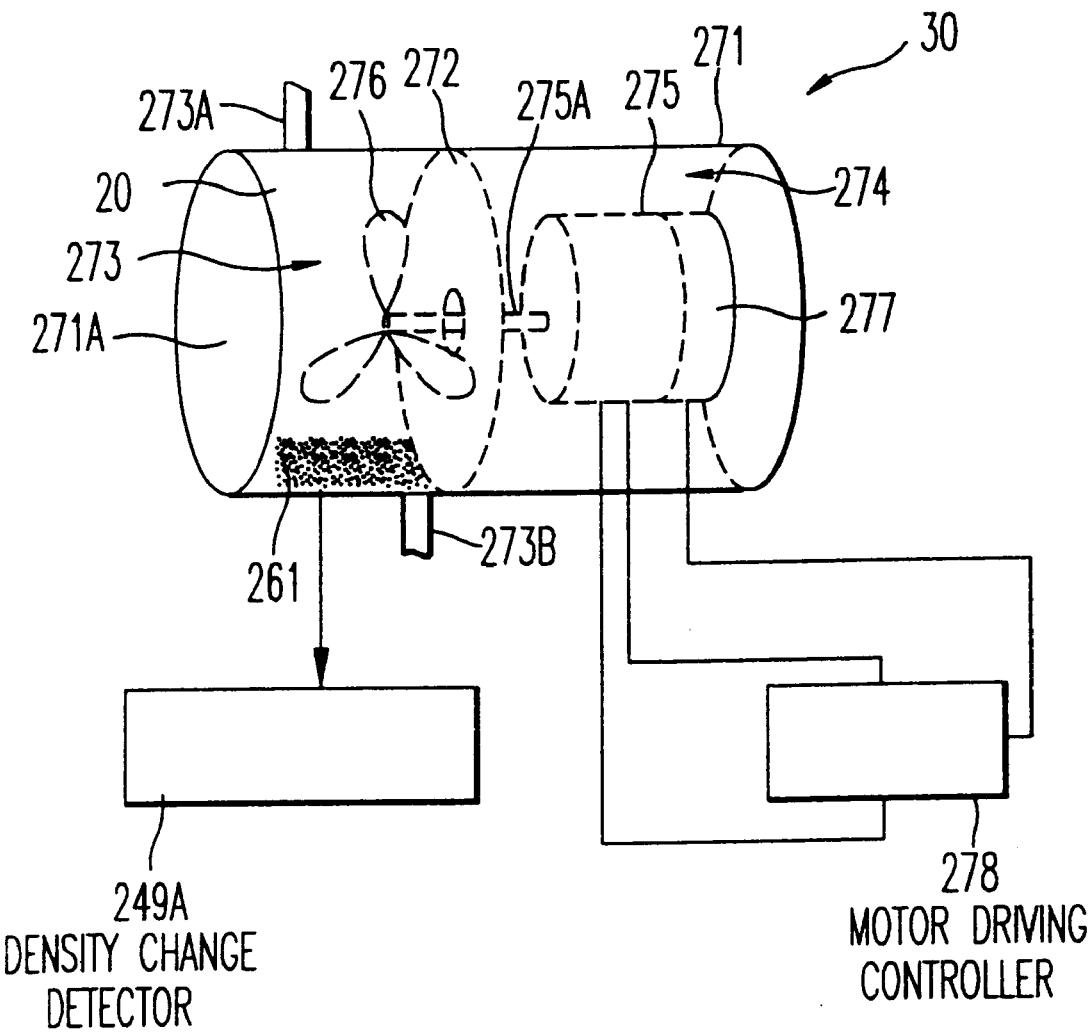
FIG. 34 is a cross sectional view of still another embodiment of the present invention in which a density is detected by measuring a pressure of a liquid type developer as an object of density detection when the liquid type developer is stirred by a fan driven by a motor which contacts the liquid type developer.

To measure a change in density in a manner as described above, a flowing detector 261 is employed in the area 273 to detect a flowing velocity of the liquid type developer 20 or pressure thereof when stirred by a fan 276 as illustrated in FIG. 34, and a DC motor 275 is controlled to rotate with a predetermined constant rotational speed. A density change detector 249b can calculate a change in density of the liquid type developer 20 contained in the area 273 based upon flowing velocity of the liquid type developer 20 or pressure thereof detected by the flowing detector 261 referring to a reference speed or reference pressure which respectively corresponds to a normal density.

A temperature controller can also be employed for controlling a temperature of a liquid type developer 20 to maintain a predetermined density of liquid type developer 20 within a predetermined range, since pressure of the liquid type developer 20 contained in the area 273 or a flowing speed thereof varies depending upon a temperature, and accordingly precise density detection is not obtained.

To resolve such a problem, a heating element and a temperature controller (not shown) can be employed in each of the density detecting device as shown in FIGS. 30, 31, 32, 33 and 34.

Obviously numerous additional modifications and variations of the present invention are possible in light of the above teachings. It is therefore to be understood that within the scope of the appended claims, the present invention may be practiced otherwise than as specifically described herein.

The present application is based on Japanese Priority Docuemnts 08-320950, 08-338944, 08-320949 and 09-177840, the contents of which are incorporated herein by reference.

What is claimed as new and desired to be secured by Letters Patent of the United States is:

1. An image forming apparatus, comprising:
    a photoconductive carrier for carrying a latent image formed by an electrophotographic process;
    a developing device for developing said latent image with a first liquid type developer composed of solid particles and a liquid type solution material;
    a liquid type developer supplying means for supplying at least one of second and third liquid type developers to said developing device;
    a developer density detecting device for detecting density of the first liquid type developer, said developer density detecting device including,
        a developer tank for storing the first liquid type developer as an object of density detection therein,
        a developer supplying device for supplying the first liquid type developer from the developing device to said developer tank,
        a developer ejecting device for ejecting the first liquid type developer from said developer tank to said developing device after density detection thereof is completed,
        a permanent magnet for forming a magnetic field around said developer tank;
        a coil for generating an induced current, said coil being disposed beside said developer tank and in said magnetic field;
        a steel ball for changing said magnetic field formed by said permanent magnet by falling through said coil from a seal of said developer tank to a bottom of said developer tank,
        a current sensor for sensing an induced current flowing in said coil when said steel ball falls through said coil;
    a viscosity calculating device for calculating viscosity based upon said current sensed by said current sensor;
    a density determining device for determining density based upon said viscosity referring to relations between viscosity of the first liquid type developer and density thereof;
    a density controller for controlling the liquid type developer supplying means to supply either the second or third liquid type developer to said developing device to maintain density of the first liquid type developer within a predetermined range, wherein the second liquid type developer is supplied to said developing device in a case that said density determining device determines density of the first liquid type developer as less than the predetermined range, and the third liquid type developer is supplied to said developing device in a case that said density determining device determines density of the first liquid type developer as greater than the predetermined range.

2. An image forming apparatus as claimed in claim 1, further comprising:
    an electromagnet for selectively attracting said steel ball to contact the seal of said developer tank and releasing said steel ball to fall from said seal into the first liquid type developer stored in said developer tank; and
    an electromagnet controller for selectively supplying electricity to said electromagnet to attract said steel ball to keep the steel ball at an initial position for density detection and stopping supplying electricity to said electromagnet to release said steel ball to fall into the first liquid type developer to execute density detection.

3. An image forming apparatus as claimed in claim 2, further comprising:
    an upper dent disposed on the seal of said developer tank for accepting said steel ball when said electromagnet attracts said steel ball.

4. An image forming apparatus as claimed in claim 1, wherein said first liquid type developer stored in said developer tank is changed after a first density detection thereof is completed by ejecting an old first liquid type developer stored in said developer tank through said developer ejecting device and supplying a new first liquid type developer from said developing device through said developer supplying device.

5. An image forming apparatus as claimed in claim 1, wherein said coil winds around said developer tank at approximately a middle height of said developer tank and said permanent magnet is positioned at a same height as said coil.

6. An image forming apparatus as claimed in claim 1, wherein said viscosity calculating device calculates viscosity based upon a maximum current induced in said coil.

7. An image forming apparatus as claimed in claim 1, wherein said viscosity calculating device calculates viscosity based upon an integral amount of current induced in said coil.

8. An image forming apparatus, comprising:
a photoconductive carrier for carrying a latent image formed by an electrophotographic process;
a developing device for developing said latent image with a first liquid type developer composed of solid particles and a liquid type solution material;
a liquid type developer supplying means for supplying second and third liquid type developers to said developing device;
a developer density detecting device for detecting density of the first liquid type developer, said developer density detecting device including,
a developer tank for storing the first liquid type developer,
a developer supplying device for supplying the first liquid type developer from said developing device to said developer tank,
a developer ejecting device for ejecting the first liquid type developer from said developer tank to said developing device after said density detection is completed,
a steel ball falling from a seal of said developer tank to a bottom thereof through the first liquid type developer stored in said developer tank,
a piezoelectric element disposed at a bottom of said developer tank for generating at least one of a voltage and a current signal when said steel ball falling from said seal collides therewith,
a timer for counting a time from which said steel ball starts falling from said seal and collides with said piezoelectric element;
a viscosity calculating device for calculating viscosity based upon the time counted by said timer;
a density determining device for determining density based upon said viscosity referring to relations between viscosity of the first liquid type developer and density thereof;
a density controller for controlling said liquid type developer supplying means to supply either the second or third liquid type developer to maintain density of the first liquid type developer within a predetermined range, wherein the second liquid type developer is supplied to said developing device in a case that said density determining device determines density of the first liquid type developer as less than the predetermined range, and the third liquid type developer is supplied in a case that said density determining device determines density of the first liquid type developer as greater than the predetermined range.

9. An image forming apparatus as claimed in claim 8, wherein said developer supplying device and said developer ejecting device are respectively composed of a pipe.

10. An image forming apparatus as claimed in claim 8, further comprising:
an electromagnet for selectively attracting said steel ball to contact said seal of said developer tank and releasing said steel ball into the first liquid type developer stored in said developer tank; and
an electromagnet controller for selectively supplying electricity to said electromagnet to attract said steel ball and keep said steel ball at an initial position for density detection or stopping supplying electricity to said electromagnet to release said steel ball to fall into the first liquid type developer for executing density detection.

11. An image forming apparatus as claimed in claim 10, wherein said developer supplying device and said developer ejecting device are made of an elastic material for allowing expanding when pulled.

12. An image forming apparatus as claimed in claim 11, wherein said electromagnet for magnetically attracting said steel ball is connected to said developer tank and integrally swings together with said developer tank.

13. An image forming apparatus as claimed in claim 10, further comprising:
a swinging device for swinging said developer tank around a horizontal axis of said developer tank to be upside down, after said steel ball kept in an upper dent starts falling into the first liquid type developer stored in said developer tank and before said steel ball reaches the bottom of said developer tank; and
said swinging device at a same time twists both said developer supplying device and said developer ejecting device to intersect each other.

14. An image forming apparatus as claimed in claim 13, wherein said upper dent is formed at approximately a middle portion of an upper wall of said developer tank.

15. An image forming apparatus as claimed in claim 13, wherein said steel ball is received by said upper dent positioned at the bottom of said developer tank swung to be upside down.

16. An image forming apparatus as claimed in claim 13, wherein said developer tank once being upside down is further swung by said swinging device to be upside down in a reverse direction to return to an initial position for density detection of said developer tank while untwisting said developer supplying device and said developer ejecting device.

17. An image forming as claimed in claim 16, wherein the first liquid type developer is changed with a new first liquid type developer by ejecting an old first liquid type developer from said developer tank through said developer ejecting pipe and supplying a new first liquid type developer from said developing device through said developer supplying device after said density determining is completed and before a next density determining starts.

18. An image forming apparatus as claimed in claim 13, further comprising:
a bottom dent disposed on a bottom of said developer tank for accepting said steel ball falling through the first liquid type developer stored in said developer tank;
a lower electromagnet disposed below said bottom dent for selectively attracting or releasing said steel ball into or from said bottom dent;
wherein said developer tank is swung with both said electromagnet and said lower electromagnet by said swinging device to be upside down while twisting said developer supplying device and said developer ejecting device to intersect each other.

19. An image forming apparatus as claimed in claim 18, wherein said electromagnet and said lower electromagnet are controlled such that if said steel ball is positioned at an initial position for density detection, electricity is supplied to said electromagnet to keep said steel ball in said upper dent, and when density detection is to be started, supplying of said electricity is stopped to release said steel ball into the first liquid type developer stored in said developer tank, and when said steel ball reaches said bottom dent, electricity is supplied to said lower electromagnet until said developer tank is swung to be upside down and a next density detection starts.

20. A developer density detecting device comprising:

a developer tank for storing a liquid type developer as an object of density detection;

a developer supplying device for supplying the liquid type developer from a developing device disposed in a developing station to said developer tank;

a developer ejecting device for ejecting the liquid type developer from said developer tank to said developing device after density detection thereof is completed;

a permanent magnet for forming a magnetic field around said developer tank;

a coil disposed beside said developer tank and in said magnetic field for generating an induced current therein;

a steel ball for changing said magnetic field formed by said permanent magnet by falling through said coil from a seal of said developer tank to a bottom thereof, said steel ball being installed in said developer tank;

a current sensor for sensing an induced current flowing in said coil when said steel ball falls through said coil;

a viscosity calculating device for calculating viscosity based upon said current sensed by said current sensor;

a density determining device for determining density based upon said viscosity referring to relations between viscosity of the liquid type developer and density thereof.

21. A developer density detecting device, comprising:

a developing device for developing latent images;

a developer tank for storing a liquid type developer;

a developer supplying device for supplying said liquid type developer from said developing device disposed in a developing station to said developer tank;

a developer ejecting device for ejecting said liquid type developer from said developer tank to said developing device after a density determination is completed;

a steel ball for falling from a seal of said developer tank to a bottom thereof through said liquid type developer stored in said developer tank;

a piezoelectric element disposed at a bottom of said developer tank for generating at least one of a voltage and a current signal when said steel ball collides therewith;

a timer for counting a time in which said steel ball starts falling from said seal and collides with said piezoelectric element at said bottom;

a viscosity calculating device for calculating viscosity based upon the time counted by said timer;

a density determining device for determining density based upon said viscosity referring to relations between viscosity of said liquid type developer and density thereof.

* * * * *